US009221840B2

(12) United States Patent
Schwiebert

(10) Patent No.: US 9,221,840 B2
(45) Date of Patent: Dec. 29, 2015

(54) TREATING PROTEIN FOLDING DISORDERS WITH SMALL MOLECULE CFTR CORRECTORS

(75) Inventor: Erik M. Schwiebert, Birmingham, AL (US)

(73) Assignee: DISCOVERYBIOMED INC., Birmingham, AL (US)

( * ) Notice: Subject to any disclaimer, the term of this patent is extended or adjusted under 35 U.S.C. 154(b) by 0 days.

(21) Appl. No.: 14/117,705

(22) PCT Filed: May 17, 2012

(86) PCT No.: PCT/US2012/038347

§ 371 (c)(1), (2), (4) Date: Nov. 14, 2013

(87) PCT Pub. No.: WO2012/158913

PCT Pub. Date: Nov. 22, 2012

(65) Prior Publication Data

US 2014/0073632 A1 Mar. 13, 2014

Related U.S. Application Data

(60) Provisional application No. 61/486,929, filed on May 17, 2011.

(51) Int. Cl.

| | |
|---|---|
| ***A61K 31/519*** | (2006.01) |
| ***C07D 513/04*** | (2006.01) |
| ***A61K 31/513*** | (2006.01) |
| ***G01N 33/50*** | (2006.01) |
| ***G01N 33/84*** | (2006.01) |
| ***C07D 239/95*** | (2006.01) |
| ***C07D 487/04*** | (2006.01) |
| ***C07D 223/04*** | (2006.01) |
| ***C07D 239/42*** | (2006.01) |
| ***C07D 241/52*** | (2006.01) |
| ***C07D 251/46*** | (2006.01) |
| ***C07D 417/04*** | (2006.01) |
| ***C07D 473/06*** | (2006.01) |

(52) U.S. Cl.

CPC ............ *C07D 513/04* (2013.01); *A61K 31/513* (2013.01); *A61K 31/519* (2013.01); *C07D 223/04* (2013.01); *C07D 239/42* (2013.01); *C07D 239/95* (2013.01); *C07D 241/52* (2013.01); *C07D 251/46* (2013.01); *C07D 417/04* (2013.01); *C07D 473/06* (2013.01); *C07D 487/04* (2013.01); *G01N 33/502* (2013.01); *G01N 33/84* (2013.01); *G01N 2800/382* (2013.01)

(58) Field of Classification Search

CPC .................................................... A61K 31/519

See application file for complete search history.

(56) References Cited

U.S. PATENT DOCUMENTS

| | | | |
|---|---|---|---|
| 5,084,457 | A | 1/1992 | Fanshawe et al. |
| 5,650,096 | A | 7/1997 | Harris et al. |
| 6,248,753 | B1 | 6/2001 | Chen |
| 2005/0209255 | A1 | 9/2005 | Jimenez et al. |
| 2007/0275986 | A1 | 11/2007 | Becq et al. |
| 2009/0048260 | A1 | 2/2009 | Becq et al. |
| 2009/0163545 | A1 | 6/2009 | Goldfarb |
| 2010/0190832 | A1 | 7/2010 | Surolia |
| 2011/0146381 | A1 | 6/2011 | Wells et al. |

FOREIGN PATENT DOCUMENTS

| | | | | |
|---|---|---|---|---|
| FR | 2116302 | | 7/1972 | |
| FR | 2910001 | | 6/2008 | |
| JP | 55066580 | A | 5/1980 | |
| SU | 1235867 | | 6/1986 | |
| WO | 98/37878 | | 9/1998 | |
| WO | 00/43373 | | 7/2000 | |
| WO | 00/61159 | | 10/2000 | |
| WO | 03/066630 | A2 | 8/2003 | |
| WO | 2004/020596 | | 3/2004 | |
| WO | 2007/044560 | | 4/2007 | |
| WO | 2009/036341 | | 3/2009 | |
| WO | 2011/046381 | A2 | 4/2011 | |
| WO | WO 2012/075393 | * | 7/2012 | ........... C07D 239/54 |
| WO | 2012/171954 | A1 | 12/2012 | |
| WO | 2012/158913 | | 1/2013 | |
| WO | 2013/052844 | | 4/2013 | |
| WO | 2014/081820 | A1 | 5/2014 | |
| WO | 2014/081821 | A2 | 5/2014 | |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975.*

Banker, Gilbert S. et al., Modem Pharmaceutics, Marcel Dekker, New York, 1996.*

Elnagdi, et al., Reactions with Heterocyclic Amidines, VII: Synthesis of Some New Pyrazolo[1,5-c]-1,2,4-triazines, Pyrazolo[1,5-a]-1,3,5-triamines and Pyrazolo[1,5-a]pyrimidines, Monatshefte fur Chemie 112, 245-252 (1981).*

(Continued)

*Primary Examiner* — Erich A Leeser

(74) *Attorney, Agent, or Firm* — Kilpatrick Townsend & Stockton, LLP

(57) ABSTRACT

Novel CFTR corrector compounds that are effective in rescuing halide efflux in a cell are provided. Also provided are methods for treating protein folding disorders (e.g., cystic fibrosis). The methods include administering a CFTR corrector compound or pharmaceutically acceptable salt or prodrug thereof. Methods of screening for CFTR corrector compounds are also described herein. The methods of screening include contacting a cell that endogenously expresses a CFTR mutation with the compound to be screened and detecting a rescue of halide efflux from the cell.

14 Claims, 4 Drawing Sheets

(56) References Cited

FOREIGN PATENT DOCUMENTS

WO 2014/152213 A2 9/2014
WO 2014/152278 A2 9/2014

OTHER PUBLICATIONS

Didenko, et al., Synthesis of 7,8-Dihydro-6H-Pyrazolo[5',1':3,4][1,2,4]-Triazino[6,5-d][1,2]Diazepin-6-one, A New Heterocyclic System, Chemistry of Heterocyclic Compounds (2009).*

Didenko, et al., Regioselective and Regiospecific Reactions of Ethyl ortho-(Dimethylaminovinylazoloazinylcarboxylates with Hydrazine, Russian J. of General Chem., vol. 80, No. 4, pp. 814-817 (2010).*

International Search Report and Written Opinion for International Application No. PCT/US2012/038347 mailed Nov. 28, 2012 (14 pages).

International Preliminary Report on Patentability for International Application No. PCT/US2012/038347 mailed Nov. 28, 2013 (11 pages).

Partial Supplementary European Search Report for EP Application No. 12785637.5 mailed Dec. 12, 2014.

Ameen et al., "Endocytic trafficking of CFTR in health and disease", Journal of Cystic Fibrosis, vol. 6, No. 1, Jan. 2007, pp. 1-14.

Anderson et al., "Chloride channels in the apical membrane of normal and cystic fibrosis airway and intestinal epithelia", American Journal of Physiology, vol. 263, No. 1, Pt 1, 1992, pp. L1-L14.

Antunes et al., "Murine nasal septa for respiratory epithelial air-liquid interface cultures", Biotechniques, vol. 43, No. 2, Aug. 2007, pp. 195-196, 198, 200 passim.

Apodaca, "Endocytic traffic in polarized epithelial cells: role of the actin and microtubule cytoskeleton", Traffic, vol. 2, No. 3, Mar. 2001, pp. 149-159.

Barker et al., "Effect of macrolides on in vivo ion transport across cystic fibrosis nasal epithelium", American journal of respiratory and critical care medicine, vol. 171, No. 8, Apr. 15, 2005, pp. 868-871.

Bartoszewski et al., "Activation of the unfolded protein response by DeltaF508 CFTR", American Journal of Respiratory Cell and Molecular Biology, vol. 39, No. 4, Oct. 2008, pp. 448-457.

Bates et al., "Membrane lateral diffusion and capture of CFTR within transient confinement zones", Biophysical Journal, vol. 91, No. 3, Aug. 1, 2006, pp. 1046-1058.

Bebok et al., "Activation of Delta- F508 CFTR in an Epithelial Monolayer", American Journal of Physiology—Cell Physiology, vol. 44, No. 2 Pt 1, Aug. 1998, pp. C599-C607.

Bebok, "Failure of cAMP agonists to activate rescued deltaF508 CFTR in CFBE41o- airway epithelial monolayers", Journal of Physiology, vol. 569, Pt. 2, Dec. 1, 2005, pp. 601-615.

Bebok et al., "The mechanism underlying CFTR transport from the endoplasmic reticulum to the proteasome includes Sec61β, and a cytosolic, deglycosylated intermediary", Journal of Biological Chemistry, vol. 273, Nov. 6, 1998, pp. 29873-29878.

Bence et al., "Impairment of the ubiquitin-proteasome system by protein aggregation", Science, vol. 292, No. 5521, May 25, 2001, pp. 1552-1555.

Blad et al., "Novem 3,6,7-Substituted Pyrazolopyrimidines as Positive Allosteric Modulators for the Hydroxycarboxylic Acid Receptor 2 (GPR109A)", Journal of Medicinal Chemistry, 2012, 55, pp. 3563-3567.

Bossard et al., "NHERF1 protein rescues DeltaF508-CFTR function", American Journal of Physiology. Lung Cellular and Molecular Physiology, vol. 292, No. 5, May 2007, pp. L1085-L1094.

Boyd et al., "Revisiting the mouse lung model for CF", Gene Therapy, vol. 11, No., 2004, pp. 737-7387.

Bradbury et al., "Biochemical and biophysical identification of cystic fibrosis transmembrane conductance regulator chloride channels as components of endocytic clathrin-coated vesicles", The Journal of Biological Chemistry, vol. 269, No. 11, Mar. 18, 1994, pp. 8296-8302.

Bubb et al., "Jasplakinolide, a cytotoxic natural product, induces actin polymerization and competitively inhibits the binding of phalloidin to F-actin", The Journal of Biological Chemistry, vol. 269, No. 21, May 27, 1994, pp. 14869-14871.

Buss et al., "How are the cellular functions of myosin VI regulated within the cell?", Biochemical and Biophysical Research Communications, vol. 369, No. 1, Apr. 25, 2008, pp. 165-175.

Carlile et al., "Correctors of protein trafficking defects indentified by a novel high-throughput screening assay", ChmBioChem 2007, 8, pp. 1012-1020.

Chen et al., "Mechanisms of cystic fibrosis transmembrane conductance regulator activation by S-nitrosoglutathione", The Journal of Biological Chemistry, vol. 281, No. 14, Apr. 7, 2006, pp. 9190-9199.

Cheng et al., "A Golgi-associated PDZ domain protein modulates cystic fibrosis transmembrane regulator plasma membrane expression", The Journal of Biological Chemistry, vol. 277, No. 5, Feb. 1, 2002, pp. 3520-3529.

Choi et al., "Synergistic airway gland mucus secretion in response to vasoactive intestinal peptide and carbachol is lost in cystic fibrosis", The Journal of Clinical Investigation, vol. 117, No. 10, Oct. 2007, pp. 3118-3127.

Chou et al., "Ziram causes dopaminergic cell damage by inhibiting E1 ligase of the proteasome", The Journal of Biological Chemistry, vol. 283, No. 50, Dec. 12, 2008, pp. 34696-34703.

Clancy et al., "No detectable improvements in cystic fibrosis transmembrane conductance regulator by nasal aminoglycosides in patients with cystic fibrosis with stop mutations", American Journal of Respiratory Cell and Molecular Biology, vol. 37, No. 1, Jul. 2007, pp. 57-66.

Clarke et al., "A domain mimic increases DeltaF508 CFTR trafficking and restores cAMP-stimulated anion secretion in cystic fibrosis epithelia", American Journal of Physiology. Cell Physiology, vol. 287, No. 1, Jul. 2004, pp. C192-C199.

Cotlin et al., "Casein Kinase II activity is required for transferrin receptor endocytosis", Journal of Biological Chemistry, vol. 274, No. 43, Oct. 22, 1999, pp. 30550-30556.

Database PubChem BioAssay, "GNF-pf-3276", retrieved from NCBI, Database accession No. CID 761910.

Eden et al., "Adaptor protein disabled-2 modulates low density lipoprotein receptor synthesis in fibroblasts from patients with autosomal recessive hypercholesterolaemia", Human Molecular Genetics, vol. 16, No. 22, Nov. 15, 2007, pp. 2751-2759.

Drabczynska et al., N9-Benzyl-substituted 1,3-dipropyl-pyrimido[2,1-f]purinediones: Synthesis and structure-activity relationships at adenosine A2 and A2A receptors. Bioorganic & Medicinal Chemistry, Jul. 6, 2007, 15, (14), pp. 5003-8017 [online], CAPLUS (STN), 2007: 617040.

Estell et al., "Plasma membrane CFTR regulates RANTES expression via its C-terminal PDZ-interacting motif", Molecular and Cellular Biology, vol. 23, No. 2, Jan. 2003, pp. 594-606.

Gentzsch et al., "Endocytic trafficking routes of wild type and DeltaF508 cystic fibrosis transmembrane conductance regulator", Molecular biology of the cell, vol. 15, No. 6, Jun. 2004, pp. 2684-2696.

Gilon et al., "Degradation signals for ubiquitin system proteolysis in Saccharomyces cerevisiae", EMBO Journal, vol. 17, No. 10, 1998, pp. 2759-2766.

Goldstein et al., "VCP/p97 AAA-ATPase Does Not Interact with the Endogenous Wild-Type Cystic Fibrosis Transmembrane Conductance Regulator", American Journal of Respiratory Cell and Molecular Biology, vol. 36, No. 6, Jun. 2007, pp. 706-714.

Gregg et al., "Pyrazolo[1,5-a]pyrimidines. Identification of the Privileged Structure and Combinational Synthesis of 3-(Hetero)arylpyrazolo[1,5-a]pyrimidine-6-carboxamides", J. Comb. Chem. 2007, 9, pp. 507-512.

Grubb et al., "Pathophysiology of gene-targeted mouse models for cystic fibrosis", Physiological Reviews, vol. 79, Suppl 1, Jan. 1999, pp. S193-S214.

Guggino et al., "Macromolecular interactions and ion transport in cystic fibrosis", American journal of respiratory and critical care medicine, vol. 170, No. 7, 2004, pp. 815-820.

(56) References Cited

OTHER PUBLICATIONS

Guggino et al., "New insights into cystic fibrosis: molecular switches that regulate CFTR", Nature Reviews. Molecular Cell Biology, vol. 7, No. 6, Jun. 2006, pp. 426-436.
Haggie et al., "Tracking of quantum dot-labeled CFTR shows near immobilization by C-terminal PDZ interactions", Molecular biology of the cell, vol. 17, No. 12, Dec. 2006, pp. 4937-4945.
Hardtmann et al., "Synthesis and Biological Evaluation of Some 10-Substituted 2,3-Dihydroimidazo[2,1-*b*]quinazolin-5(10*H*)-ones, a New Class of Bronchodilators", Journal of Medical Chemistry, vol. 18, No. 5, May 1975, pp. 447-453.
Heasman et al., "Mammalian Rho GTPases: new insights into their functions from in vivo studies", Nature Reviews—Molecular Cell Biology, vol. 9, No. 9, Sep. 2008, pp. 690-701.
Heda et al., "The ΔF508 mutation shortens the biochemical half-life of plasma membrane CFTR in polarized epithelial cells", American Journal of Physiology—Cell Physiology, vol. 280, Jan. 1, 2001, pp. C166-C174.
Ianowski et al., "Mucus secretion by single tracheal submucosal glands from normal and cystic fibrosis transmembrane conductance regulator knockout mice", Journal of Physiology, vol. 580, Pt. 1, Apr. 1, 2007, pp. 301-314.
Ishikura et al., "Small G proteins in insulin action: Rab and Rho families at the crossroads of signal transduction and GLUT4 vesicle traffic", Acta Physiologica, vol. 192, No. 1, 2008, pp. 61-74.
Jin et al., "Single-particle tracking of membrane protein diffusion in a potential: simulation, detection, and application to confined diffusion of CFTR Cl- channels", Biophysical Journal, vol. 93, No. 3, Aug. 1, 2007, pp. 1079-1088.
Jurkuvenaite et al., "Mutations in the Amino Terminus of the Cystic Fibrosis Transmembrane Conductance Regulator Enhance Endocytosis", The Journal of Biological Chemistry, vol. 281, No. 6, Feb. 2006, pp. 3329-3334.
Koller et al., "Toward an animal model of cystic fibrosis: targeted interruption of exon 10 of the cystic fibrosis transmembrane regulator gene in embryonic stem cells", PNAS, vol. 88, No. 23, Dec. 1991, pp. 10730-10734.
Korzycka et al., "Synthesis and pharmacological investigations of new 6-oxo-1,2,3,4-tetrahydro-6H-pyrimido[2,1-b] quinazolilne derivatives", Pharmazie vol. 49, No. 11 (1994), pp. 815-819.
Kowanetz et al., "Identification of a novel proline-arginine motif involved in CIN85-dependent clustering of Cbl and down-regulation of epidermal growth factor receptors", The Journal of Biological Chemistry, vol. 278, No. 41, Oct. 10, 2003, pp. 39735-39746.
Kozhushko et al., Database CA, "2-(o-Carboxyphenylamino)-6-H-pyrimido[2,1-b]quinazol-6-one ester hydrochlorides with anti-inflammatory, analgesic, and antipyretic activity", retrieved from STN, Dabase accession No. 1988:143464.
Kwon et al., "Knockdown of NHERF1 enhances degradation of temperature rescued DeltaF508 CFTR from the cell surface of human airway cells", Cellular Physiology and Biochemistry, vol. 20, No. 6, Feb. 2007, pp. 763-772.
Lack et al., Targeting the Binding Function 3 (BF3) Site of the Human Androgen Receptor through Virtual Screening. Journal of Medicinal Chemistry, Dec. 22, 2011, 54, (24), pp. 8563-8573 [online], CAS (STN), 156:139523, RN 1351360-62-7.
Laddha et al., "A new therapeutic approach in Parkinson's disease: Some novel quinazoline derivatives as dual selective phosphodiesterase 1 inhibitors and anti-inflammatory agents",Bioorganic & Medicinal Chemistry 17 (2009), pp. 6796-6802.
Leung, "Modulation of endocytic traffic in polarized Madin-Darby canine kidney cells by the small GTPase RhoA", Molecular biology of the cell, vol. 10, No. 12, Dec. 1999, pp. 4369-4384.
Lukacs et al., "Conformational maturation of CFTR but not its mutant counterpart (delta F508) occurs in the endoplasmic reticulum and requires ATP", EMBO Journal, vol. 13, No. 24, Dec. 15, 1994, pp. 6076-6086.
Lukacs et al., "Constitutive internalization of cystic fibrosis transmembrane conductance regulator occurs via clathrin-dependent endocytosis and is regulated by protein phosphorylation", The Biochemical journal, vol. 328, Pt 2, Dec. 1, 1997, pp. 353-361.
Matsui et al., "Evidence for periciliary liquid layer depletion, not abnormal ion composition, in the pathogenesis of cystic fibrosis airways disease", Cell, vol. 95, No. 7, Dec. 23, 1998, pp. 1005-1015.
Mazzochi et al., "Interaction of epithelial ion channels with the actinbased cytoskeleton", American Journal of Physiology—Renal Physiology, vol. 291, No. 6, Dec. 2006, pp. F1113-F1122.
Mitra et al., "RNAi-based analysis of CAP, Cbl, and Crkll function in the regulation of GLUT4 by insulin", The Journal of Biological Chemistry, vol. 279, No. 36, Sep. 3, 2004, pp. 37431-37435.
Morris et al., "Myosin VI binds to and localises with Dab2, potentially linking receptor-mediated endocytosis and the actin cytoskeleton", Traffic, vol. 3, No. 5, May 2002, pp. 331-341.
Naren et al., "A macromolecular complex of beta 2 adrenergic receptor, CFTR, and ezrin/radixin/moesin-binding phosphoprotein 50 is regulated by PKA", PNAS, vol. 100, No. 1, Jan. 7, 2003, pp. 342-346.
NCBI, PubChem Compound, CID 2806960, Create Date: Jul. 19, 2005.
NCBI, PubChem Compound, CID 16417802, Create Date: Jul. 31, 2007.
Okiyoneda, "Cell surface dynamics of CFTR: the ins and outs", Biochimica et Biophysica Acta (BBA)—Molecular Cell Research, vol. 1773, No. 4, Apr. 2007, pp. 476-479.
Pastva et al., "Aerobic exercise attenuates airway inflammatory responses in a mouse model of atopic asthma", Journal of Immunology, vol. 172, No. 7, Apr. 1, 2004, pp. 4520-4526.
Peter et al., "Ablation of internalization signals in the carboxyl-terminal tail of the cystic fibrosis transmembrane conductance regulator enhances cell surface expression", The Journal of Biological Chemistry, vol. 277, No. 51, Dec. 20, 2002, pp. 49952-49957.
Picciano et al., "Rme-1 regulates the recycling of the cystic fibrosis transmembrane conductance regulator", American Journal of Physiology—Cell Physiology, vol. 285, 2003, pp. C1009-C1018.
Prince et al., "Efficient endocytosis of the cystic fibrosis transmembrane conductance regulator requires a tyrosine-based signal", Journal of Biological Chemistry, vol. 274, No. 6, Feb. 5, 1999, pp. 3602-3609.
Prince et al., "Rapid endocytosis of the cystic fibrosis transmembrane conductance regulator chloride channel", PNAS, vol. 91, No. 11, May 24, 1994, pp. 5192-5196.
Rab et al., "Endoplasmic Reticulum Stress and The Unfolded Protein Response Regulate Genomic Cystic Fibrosis Transmembrane Conductance Regulator Expression", American Journal of Physiology—Cell Physiology, vol. 292, No. 2, Feb. 2006, pp. C756-C766.
Rao et al., "The Cbl family of ubiquitin ligases: critical negative regulators of tyrosine kinase signaling in the immune system", Journal of Leukocyte Biology, vol. 71, No. 5, May 2002, pp. 753-763.
Robelet et al., Pharmacological effects of some 8-substituted theophylline derivatives. Journal de Physiologie (Paris, 1946-1992), 57, 389-90 From: CZ 1966, (47), Abstr. No. 1736, 1965 [online], CAS (STN), 67:20141.
Romanenko et al., Syntehsis and physicochemical properties of 1-methyl-6,7,8,9-tetrahydropyrimido[2,1-f]xanthine derivatives. Ukrainskii Khimicheskii Zhurnal (Russian Edition), 1994, 60, 3-4, pp. 300-302 (abstract) [online] CAPLUS (STN), 1995:527572.
Romanenko et al., The synthesis and pharmacological activity of the derivatives of 1-methyl-3H-6,9-dihydro-1,2,4-triazino[3,4-f]xanthine. Khimico-Farmatsevticheskii Zhurnal, 1986, 20(2), 187-190 (abstract) [online] CAS (STN), 106:84528, RN 106087-29-0P, 106087-30-3P, 106087-31-4P.
Salaheldin et al., "Studies with Enaminonitriles : Synthesis and Chemical Reactivity of 2-Phenyl-3-Piperidin-1-yl Acrylonitrile under Microwave Heating", J. Heterocyclic Chem., 45, pp. 307-310 (2008).
Samura, "Effect of some imidazo[1,2-f]xanthine derivatives on bioelectrical activity and evoked potential of the cerebral hemisphere cortex", Farmakologiya I Toksikologiya, Feb. 28, 1983, 46(1), pp. 17-20 [online], STN, 1983: 101083.
Sato et al., "Glycerol reverses the misfolding phenotype of the most common cystic fibrosis mutation", Journal of Biological Chemistry, vol. 271, No. 2, Jan. 12, 1996, pp. 635-638.

(56) References Cited

OTHER PUBLICATIONS

Schroder et al., "ER stress and the unfolded protein response", Mutation Research, vol. 569, Jan. 26, 2005, pp. 29-63.
Schroder et al., "The Mammalian Unfolded Protein Response", Annual Review of Biochemistry, vol. 74, 2005, pp. 739-789.
Schultz et al., "Pharmacology of CFTR Chloride Channel Activity," Physiological Reviews, vol. 79, Suppl., No. 1, Jan. 1999, pp. S109-S144.
Schwiebert et al., "CFTR is a conductance regulator as well as a chloride channel", Physiological Reviews, vol. 79, 1999, pp. S145-S166.
Sharma et al., "Conformational and temperature-sensitive stability defects of the DF508 cystic fibrosis transmembrane conductance regulator in post-endoplasmic reticulum compartments", Journal of Biological Chemistry, vol. 276, 2001, pp. 8942-8950.
Sharma et al., "Misfolding diverts CFTR from recycling to degradation: quality control at early endosomes", Journal of Cell Biology, vol. 164, No. 6, Mar. 15, 2004, pp. 923-933.
Shen et al., Discoery of pyrazolopyrimidines as the first class of allosteric agonists for the high affinity nicotinic acid receptor GPR109A. Bioorganic & Medical Chemistry Letters, 2008, 18, pp. 4948-4951.
Short et al., "An apical PDZ protein anchors the cystic fibrosis transmembrane conductance regulator to the cytoskeleton", The Journal of Biological Chemistry, vol. 273, No. 31, Jul. 31, 1998, pp. 19797-19801.
Shumay et al., "Lysophosphatidic acid regulates trafficking of beta 2-adrenergic receptors:the Galpha 13/p115RHOGEF/JNK pathway stimulates receptor internalization", Journal of Biological Chemistry, vol. 282, No. 29, 2007, pp. 21529-21541.
Snouwaert et al., "An animal model for cystic fibrosis made by gene targeting", Science, vol. 257, No. 5073, Aug. 21, 1992, pp. 1083-1088.
STN, Registry, Jun. 24, 2008, compound with RN 1030421-22-7.
STN, Registry, Nov. 20, 2009, compound with RN 1192977-94-8.
STN, Registry, Jul. 10, 2007, RN 941951-07-01.
STN, Registry, Oct. 5, 2007, RN 949247-18-1.
STN, Registry, Oct. 5, 2007, RN 941951-03-7.
STN, Registry, Aug. 8, 2006, RN 899737-99-6.
STN, Registry, Aug. 9, 2006, RN 899998-08-4.
STN, Registry, Aug. 9, 2006, RN 899948-04-0.
STN, Registry, Aug. 9, 2006, RN 899948-08-4.
STN, Registry, Aug. 8, 2006, RN 899738-02-4.
STN, Registry, Aug. 9, 2006, RN 899998-18-6.
STN, Registry, Aug. 9, 2006, RN 899948-10-8.
STN, Registry, Jun. 25, 2008, RN 1030569-95-9.
STN, Registry, Jun. 25, 2008, RN 1030480-38-6.
STN, Registry, Jun. 25, 2008, RN 1030480-33-1.
STN, Registry, Jun. 24, 2008, RN 1030450-60-2.
STN, Registry, Jun. 24, 2008, RN 1015553-18-0.
STN, Registry, Jun. 25, 2008, RN 1030523-95-5.
STN, Registry, Jun. 25, 2008, RN 1030672-54-8.
STN, Registry, Jun. 24, 2008, RN 1030450-84-0.
STN, Registry, Aug. 23, 2006, RN 903852-54-0.
STN, Registry, Dec. 20, 2004, RN 799824-17-2.
Swiatecka-Urban et al., "Myosin Vb is required for trafficking of the cystic fibrosis transmembrane conductance regulator in Rab11a-specific apical recycling endosomes in polarized human airway epithelial cells", The Journal of Biological Chemistry, vol. 282, Aug. 10, 2007, pp. 23725-23736.
Swiatecka-Urban et al., "Myosin VI regulates endocytosis of the cystic fibrosis transmembrane conductance regulator", The Journal of Biological Chemistry, vol. 279, Sep. 3, 2004, pp. 38025-38031.
Swiatecka-Urban et al., "PDZ domain interaction controls the endocytic recycling of the cystic fibrosis transmembrane conductance regulator", Journal of Biological Chemistry, vol. 277, No. 42, Oct. 18, 2002, pp. 40099-40105.
Swiatecka-Urban et al., "The short apical membrane half-life of rescued {Delta}F508-cystic fibrosis transmembrane conductance regulator (CFTR) results from accelerated endocytosis of {Delta}F508-CFTR in polarized human airway epithelial cells", The Journal of Biological Chemistry, vol. 280, No. 44, Nov. 4, 2005, pp. 36762-36772.
Symons et al., "Control of vesicular trafficking by Rho GTPases", Current Biology, vol. 13, No. 10, May 13, 2003, pp. R409-R418.
Tarran et al., "Regulation of murine airway surface liquid volume by CFTR and Ca2+-activated Clconductances", Journal of General Physiology, vol. 120, No. 3, Sep. 2002, pp. 407-418.
Tarran et al., "Soluble mediators, not cilia, determine airway surface liquid volume in normal and cystic fibrosis superficial airway epithelia", Journal of General Physiology, vol. 127, No. 5, May 2006, pp. 591-604.
Touitou, "A degradation signal located in the C-terminus of p21WAF1/CIP1 is a binding site for the C8 alpha-subunit of the 20S proteasome", EMBO Journal, vol. 20, No. 10, May 15, 2001, pp. 2367-2375.
Tripathi et al., "CHIP chaperones wild type p53 tumor suppressor protein", The Journal of Biological Chemistry, vol. 282, No. 39, Sep. 28, 2007, pp. 28441-28454.
Tripathi et al., "Cullin4B/E3-ubiquitin ligase negatively regulates betacatenin", Journal of Biosciences, vol. 32, No. 6, Sep. 2007, pp. 1133-1138.
Tucker et al., "Transient transfection of polarized epithelial monolayers with CFTR and reporter genes using efficacious lipids", American Journal of Physiology, Cell Physiology, vol. 284, 2003, pp. C791-C804.
Van Goor et al., "Rescue of ΔF508-CFTR trafficking and gating in human cystic fibrosis airway primary cultures by small molecules", Am J Physiol Lung Cell Mol Physiol 290: 2006, pp. L1117-L1130.
Varga et al., "Efficient intracellular processing of the endogenous cystic fibrosis transmembrane conductance regulator in epithelial cell lines", The Journal of Biological Chemistry, vol. 279, No. 21, May 21, 2004, pp. 22578-22584.
Varga et al., "Enhanced cell-surface stability of rescued DeltaF508 cystic fibrosis transmembrane conductance regulator (CFTR) by pharmacological chaperones", The Biochemical journal, vol. 410, No. 3, Mar. 15, 2008, pp. 555-564.
Vij et al., "Selective inhibition of endoplasmic reticulum-associated degradation rescues DeltaF508-cystic fibrosis transmembrane regulator and suppresses interleukin-8 levels: therapeutic implications", The Journal of Biological Chemistry, vol. 281, No. 25, Jun. 23, 2006, pp. 17369-17378.
Wang et al., "Chemical and biological folding contribute to temperature-sensitive DeltaF508 CFTR trafficking", Traffic, vol. 9, No. 11, Nov. 2008, pp. 1878-1893.
Wang et al., "Hsp90 cochaperone Aha1 downregulation rescues misfolding of CFTR in cystic fibrosis", Cell, vol. 127, No. 4, Nov. 17, 2006, pp. 803-815.
Wang et al., "Reversible silencing of CFTR chloride channels by glutathionylation", Journal of General Physiology, vol. 125, No. 2, Feb. 2005, pp. 127-141.
Ward et al., "Degradation of CFTR by the ubiquitin-proteasome pathway", Cell, vol. 83, No. 1, Oct. 6, 1995, pp. 121-127.
Weixel et al., "Mu 2 binding directs the cystic fibrosis transmembrane conductance regulator to the clathrin-mediated endocytic pathway", The Journal of Biological Chemistry, vol. 276, No. 49, Dec. 7, 2001, pp. 46251-46259.
Wilschanski et al., "A pilot study of the effect of gentamicin on nasal potential difference measurements in cystic fibrosis patients carrying stop mutations", American journal of respiratory and critical care medicine, vol. 161, No. 3 Pt. 1, Mar. 2000, pp. 860-865.
Wilschanski et al., "Gentamicin-induced correction of CFTR function in patients with cystic fibrosis and CFTR stop mutations", The New England Journal of Medicine, vol. 349, No. 15, Oct. 9, 2003, pp. 1433-1441.
Wolde et al., "Targeting CAL as a negative regulator of DeltaF508-CFTR cell-surface expression: an RNA interference and structure-based mutagenetic approach", The Journal of Biological Chemistry, vol. 282, No. 11, Mar. 16, 2007, pp. 8099-8109.
Li-Na Xu et al., "Identification of Natural Coumarin Compounds that Rescue Defective AF508-CFTR Chloride Channel Gating", Clinical and Experimental Pharmacology and Physiology (2008) 35, 878-883.

(56) References Cited

OTHER PUBLICATIONS

Yang et al., "Inhibitors of ubiquitin-activating enzyme (E1), a new class of potential cancer therapeutics", Cancer Research, vol. 67, No. 19, Oct. 1, 2007, pp. 9472-9481.
Yoneda et al., Synthesis of xanthines by dehydrogenative cyclization of 6-amino-5-benylideneaminouracils with diethyl azodicarboxylate. Chemical & Pharaceutical Bulletin, 1978, 26(9), 2905-2910 (abstract) [online] CAS (STN), 90:22975.
Zeiher et al., "A mouse model for the delta F508 allele of cystic fibrosis", The Journal of Clinical Investigation, vol. 96, No. 4, Oct. 1995, pp. 2051-2064.
Zhou et al., "Nedd4-2 catalyzes ubiquitination and degradation of cell surface ENaC", The Journal of Biological Chemistry, vol. 282, No. 28, Jul. 13, 2007, pp. 20207-20212.
Zsembery et al., "Extracellular zinc and ATP restore chloride secretion across cystic fibrosis airway epithelia by triggering calcium entry", Journal of Biological Chemistry, vol. 279, No. 11, Mar. 12, 2004, pp. 10720-10729.
Alonso et al., "Competitive intramolecular nucleophilic aromatic substitution: a new route to coumarins," Chem. Commun., 2001, 639-640.
Amaral, "Therapy through chaperones: sense or antisense? Cystic fibrosis as a model disease", Journal of Inherited Metabolic Disease, vol. 29, No. 2-3, 2006, pp. 477-487.
Anderson et al., "Demonstration that CFTR is a chloride channel by alteration of its anion selectivity", Science, vol. 253, No. 5016, 1991, pp. 202-205.
Cheng et al., "Defective intracellular transport and processing of CFTR is the molecular basis of most cystic fibrosis", Cell, vol. 63, No. 4, Nov. 16, 1990, pp. 827-834.
Cheng et al., "Functional activation of the cystic fibrosis trafficking mutant delta F508-CFTR by overexpression", American Journal of Physiology, vol. 268, No. 4 Pt. 1, Apr. 1995, pp. L615-L624.
Coux et al., "Structure and functions of the 20S and 26S proteasomes", Annual Review of Biochemistry, vol. 65, 1996, pp. 801-847.
Cushing et al., "The relative binding affinities of PDZ partners for CFTR: a biochemical basis for efficient endocytic recycling", Biochemistry, vol. 47, No. 38, 2008, pp. 10084-10098.
Davidson et al., "Mouse models of cystic fibrosis", Trends in Genetics, vol. 17, No. 10, Oct. 2001, pp. S29-S37.
Davidson et al., "The CF mouse: An Important Tool for Studying Cystic Fibrosis", Expert Reviews in Molecular Medicine, vol. 2001, Mar. 2001, pp. 1-27.
Denning et al., "Processing of mutant cystic fibrosis transmembrane conductance regulator is temperature-sensitive", Nature, vol. 358, No. 6389, 1992, pp. 761-764.
Desai et al., "A convenient, rapid and eco-friendly synthesis of isoxazoline heterocyclic moiety containing bridge at 2°-amine as potential pharmacological agent", Journal of the Iranian Chemical Society, 2005, 5(1), pp. 67-73 (abstract) [online] CAS (STN), 150:237474, RN 1115854-28-8, RN 1115854-38-0, RN 1115854-41-5, RN 1115854-40-4.
Gonda, "The ascent of pulmonary drug delivery", J. Pharm. Sci. 89: 940-945, 2000.
Hanmantgad et al., "Biomimetic thiazolyl coumarins" National Academy Science Letters, 1984, 7(3), pp. 77-78 (abstract) [online] CAS (STN), 103:53986, compound of the formula I, RN: 97268-10-5.
Hunter et al., "Ubiquitin-proteasome system alterations in a striatal cell model of huntington's disease", Journal of Neuroscience Research, vol. 85, No. 8, Jun. 2007, pp. 1774-1788.
Hyde et al., "Structural model of ATP-binding proteins associated with cystic fibrosis, multidrug resistance and bacterial transport", Nature, vol. 346, No. 6282, Jul. 26, 1990, pp. 362-365.
Jensen et al., "Multiple proteolytic systems, including the proteasome, contribute to CFTR processing", Cell, vol. 83, No. 1, Oct. 6, 1995, pp. 129-135.
Kirk, "New paradigms of CFTR chloride channel regulation", Cellular and Molecular Life Sciences, vol. 57, No. 4, 2000, pp. 623-634.
Knowles et al., "Abnormal ion permeation through cystic fibrosis respiratory epithelium", Science, vol. 221, No. 4615, Sep. 9, 1983, pp. 1067-1070.
Kowanetz et al., "Dab2 links CIN85 with clathrin-mediated receptor internalization", FEBS Letters, vol. 554, No. 1-2, Nov. 6, 2003, pp. 81-87.
Kunzelmann et al., "An immortalized cystic fibrosis tracheal epithelial cell line homozygous for the delta F508 CFTR mutation", American Journal of Respiratory Cell and Molecular Biology, vol. 8, No. 5, 1993, pp. 522-529.
Lechner et al., "A serum-free method for culturing. normal human epithelial cells at clonal density", Journal of Tissue Culture Methods, vol. 9, No. 2, 1985, pp. 43-48.
Logan et al., "Cationic lipids for reporter gene and CFTR transfer to rat pulmonary epithelium", Gene Therapy, vol. 2, No. 1, Jan. 1995, pp. 38-49.
Meacham et al., "The Hsc70 co-chaperone CHIP targets immature CFTR for proteasomal degradation", Nature Cell Biology, vol. 3, No. 1, Jan. 2001, pp. 100-105.
Mori et al., "A Combination Strategy to Inhibit Pim-1: Synergism between Noncompetitive and ATP-Competitive Inhibitors", ChemMedChem, Feb. 22, 2013, 8(3), pp. 484-496, (abstract) [online] CAS (STN), RN 685551-02-4, RN 526186-61-8.
Panigrahi et al. 4-)3'-Coumarinyl)-2-arylaminothiazoles and some of their derivatives, Journal of the Indiana Chemical Society, 1971, 48(7), pp. 665-668 (abstract) [online] CAS (STN), 75:129705, RN 33856-02-9, RN 33856-03-0, RN 33856-04-1, RN 33856-05-2, RN 33856-06-3, RN 33856-07-4, RN 34560-08-2.
Pastva et al., "RU486 blocks the anti-inflammatory effects of exercise in a murine model of allergen-induced pulmonary inflammation", Brain, Behavior, and Immunity, vol. 19, No. 5, Sep. 2005, pp. 413-422.
Ratjen et al., "Cystic fibrosis", Lancet, vol. 361, No. 9358, Feb. 22, 2003, pp. 681-689.
Riordan et al., "Identification of the cystic fibrosis gene: cloning and characterization of complementary DNA", [published erratum appears in Science Sep. 29, 1989; 245(4925):1437]. Science, vol. 245, 1989, pp. 1066-1073.
Rubenstein et al., "Clinical trials of 4-phenylbutyrate for correction of sweet duct abnormalities in DF508 homozygous cystic fibrosis patients", Pediatric Pulmonary, Suppl. 13, 1996, p. 259.
Sorscher et al., "Gene therapy for cystic fibrosis using cationic liposome mediated gene transfer: a phase I trial of safety and efficacy in the nasal airway", Human Gene Therapy, vol. 5, No. 10, Oct. 1994, pp. 1259-1277.
Soubeyran et al., "Cbl-CIN85-endophilin complex mediates ligand-induced downregulation of EGF receptors", Nature, vol. 416, No. 6877, Mar. 14, 2002, pp. 183-187.
Spector et al., "Latrunculins: novel marine toxins that disrupt microfilament organization in cultured cells", Science, vol. 219, No. 4584, Feb. 4, 1983, pp. 493-495.
Srimanth et al., "Synthesis of some new types of thiazolyl coumarins", Indian Journal of Chemistry, 1999, vol. 38B, No. 4, pp. 473-475 (abstract) [online] CAS (STN), 131:228681, RN 244104-97-0.
Van Ginkel et al., "Adenoviral gene delivery elicits distinct pulmonary-associated T helper cell responses to the vector and to its transgene", Journal of Immunology, vol. 159, No. 2, Jul. 15, 1997, pp. 685-693.
Van Goor et al., "Rescue of deltaF508-CFTR Function by Small Molecules in Human Bronchial Epithelial Isolated from CF Patients", Pediatric Pulmonology, vol. 38, 2004, p. 247.
Venugopala et al., Synthesis and evaluations of some substituted 2-arylamino coumarinyl thiazoles as potential NSAIDs. Asian Journal of Chemistry, 16(2), pp. 872-876 (abstract), 2004 [online] CAS (STN), 142:219187, RN 33856-02-9, RN 33856-03-0, RN 33856-04-1, RN 33856-06-3, RN 97268-08-1, RN 97268-09-2, RN 313668-62-1, RN 325805-75-2, RN 33856-02-9.

(56) References Cited

OTHER PUBLICATIONS

Weixel et al., "Endocytic adaptor complexes bind the C-terminal domain of CFTR", Pflügers Archiv—European Journal of Physiology, vol. 443, Suppl. 1, Feb. 2001, pp. S70-S74.
Woodworth et al., "Murine tracheal and nasal septal epithelium for air-liquid interface cultures: a comparative study", American Journal of Rhinology, vol. 21, No. 5, Sep./Oct. 2007, pp. 533-537.
Yang et al., "Stimulation of Airway and Intestinal Mucosal Secretion by Natural Coumarin CFTR Activators", Frontiers in Pharmacology, 2011, 2:52 [online] [retrieved Sep. 17, 2014] Retrieved from the Internet.
Extended European Search Report for EP Application No. 12785637.5 mailed Mar. 30, 2015.
[Online] Registry via STN, Jan. 15, 2001, RN 313954-56-2.
[Online] Registry via STN, Jan. 15, 2001, RN 313954-55-1.
[Online] Registry via STN, Aug. 10, 2004, RN 724744-64-3.
[Online] Registry via STN, Apr. 3, 2002, RN 403721-74-4.
[Online] Registry via STN, Apr. 3, 2002, RN 403721-73-3.
[Online] Registry via STN, Mar. 6, 2001, RN 325804-07-7.
[Online] Registry via STN, Mar. 3, 2001, RN 325804-06-6.
[Online] Registry via STN, Mar. 4, 2001, RN 325473-18-5.
[Online] Registry via STN, Jan. 4, 2001, RN 312703-21-2.

* cited by examiner

TREATING PROTEIN FOLDING DISORDERS WITH SMALL MOLECULE CFTR CORRECTORS

CROSS-REFERENCE TO PRIORITY APPLICATIONS

This application claims priority to U.S. Provisional Application No. 61/486,929, filed May 17, 2011, which is incorporated herein by reference in its entirety.

STATEMENT REGARDING FEDERALLY FUNDED RESEARCH

This invention was made with government support under Grant Nos. NIDDK R01 DK060065 and NIDDK Phase I SBIR DK084658 awarded by the National Institutes of Health. The government has certain rights in the invention.

BACKGROUND

Cystic fibrosis is an example of a protein folding disorder. It is a hereditary disease caused by mutations in a gene encoding the cystic fibrosis transmembrane conductance regulator (CFTR). The CFTR gene encodes a chloride channel that is expressed in multiple epithelial cell types. A common CFTR mutation, delF508, causes the failure of CFTR to traffic correctly to the plasma membrane because of protein misfolding. The delF508 mutation is estimated to account for 90% of mutant alleles. Because of its high degree of incidence in the cystic fibrosis population, delF508-CFTR is a prime target for cystic fibrosis therapeutics. As such, delF508-CFTR has been extensively studied and is a model for the study of protein folding diseases.

SUMMARY

Compounds and methods for the treatment of protein folding disorders are provided. Cystic fibrosis (CF) is used throughout as an example of such a protein folding disorder. The methods include administering to a subject a CFTR corrector (i.e., a compound effective in rescuing halide efflux in a cell).

A class of CFTR correctors includes compounds of the following structure:

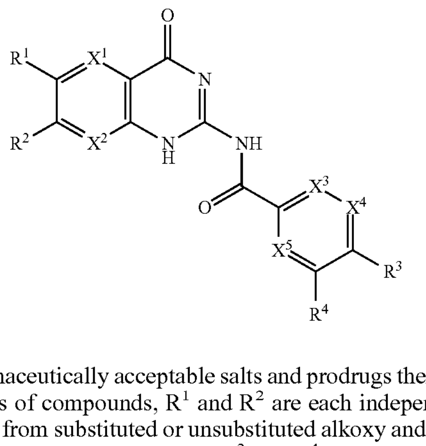

or pharmaceutically acceptable salts and prodrugs thereof. In this class of compounds, $R^1$ and $R^2$ are each independently selected from substituted or unsubstituted alkoxy and substituted or unsubstituted aryloxy; $R^3$ and $R^4$ are each independently selected from hydrogen, halogen, nitro, hydroxyl, substituted or unsubstituted alkoxy, substituted or unsubstituted aryloxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl; and $X^1$, $X^2$, $X^3$, $X^4$, and $X^5$ are each independently selected from CH and N. In this class of compounds, if $X^1$, $X^2$, $X^3$, $X^4$, and $X^5$ are each CH, $R^1$ and $R^2$ are methoxy, and $R^4$ is hydrogen, then $R^3$ is not hydrogen or chloro.

A class of CFTR correctors includes compounds of the following structure:

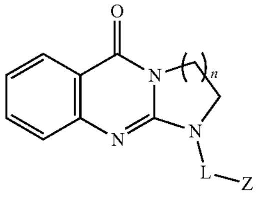

or pharmaceutically acceptable salts or prodrugs thereof. In this class of compounds, L is $-CH_2-$, $-CH_2-CH_2-$, C=O, or absent; n is 1 or 2; and Z is hydrogen, methyl, or substituted or unsubstituted aryl. Optionally, L is $-CH_2-$. Optionally, L is $-CH_2-CH_2-$. Optionally, Z is substituted or unsubstituted aryl.

Also described herein are methods for the treatment of a protein folding disorder in a subject comprising administering to the subject a compound of the following structure:

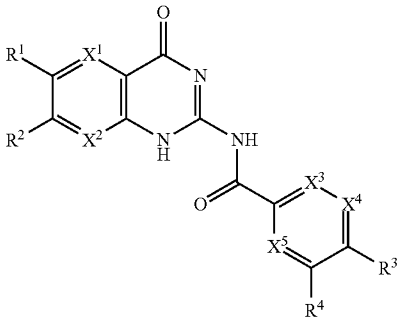

or pharmaceutically acceptable salts or prodrugs thereof. In this class of compounds, $R^1$, $R^2$, $R^3$, and $R^4$ are each independently selected from hydrogen, halogen, nitro, hydroxyl, substituted or unsubstituted alkoxy, substituted or unsubstituted aryloxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl; and $X^1$, $X^2$, $X^3$, $X^4$, and $X^5$ are each independently selected from CH and N. Optionally, $R^1$ and $R^2$ are methoxy. Optionally, $R^3$ is chloro. Optionally, $X^1$, $X^2$, $X^3$, $X^4$, and $X^5$ are CH.

In some examples, the compound is:

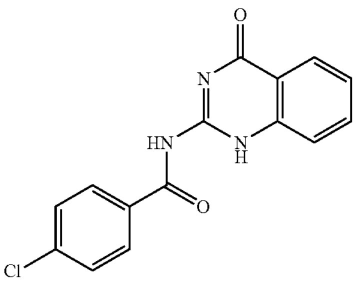

,

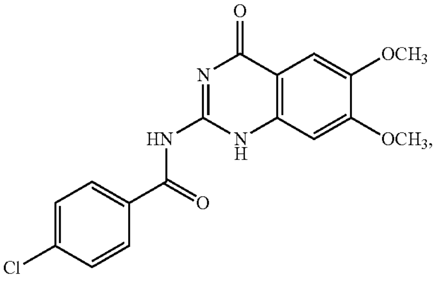

,

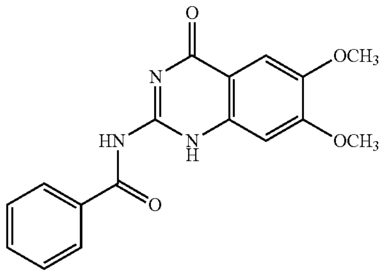

or pharmaceutically acceptable salts or prodrugs thereof.

A method for the treatment of a protein folding disorder in a subject comprises administering to the subject a compound of the following structure:

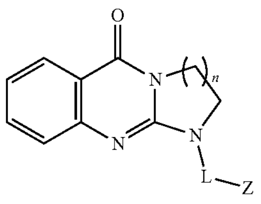

and pharmaceutically acceptable salts or prodrugs thereof. In this class of compounds, L is $-CH_2-$, $-CH_2-CH_2-$, C=O, or absent; n is 1 or 2; and Z is hydrogen, methyl, or substituted or unsubstituted aryl. Optionally, L is $-CH_2-$ or $-CH_2-CH_2-$. Optionally, Z is substituted or unsubstituted aryl.

A method for the treatment of a protein folding disorder in a subject comprises administering to the subject a compound of the following structure:

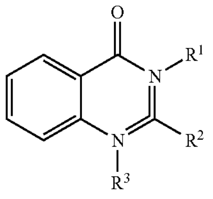

or pharmaceutically acceptable salts or prodrugs thereof. In this class of compounds, $R^1$ and $R^3$ are independently absent or each independently selected from hydrogen or substituted or unsubstituted alkyl; $R^2$ is substituted or unsubstituted amino, substituted or unsubstituted thio, or substituted or unsubstituted heterocycloalkyl; and ---- is a single bond or double bond, wherein two double bonds are not adjacent. Optionally, $R^1$ and $R^2$ are combined to form a substituted or unsubstituted aryl or substituted or unsubstituted heteroaryl.

A method for the treatment of a protein folding disorder in a subject comprises administering to the subject a compound of the following structure:

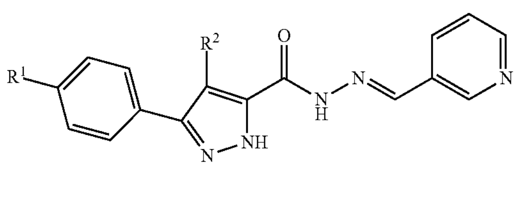

or pharmaceutically acceptable salts or prodrugs thereof. In this class of compounds, $R^1$ is hydrogen, halogen, alkoxy, or substituted or unsubstituted alkyl; and $R^2$ is hydrogen or substituted or unsubstituted alkyl. Optionally, $R^1$ is ethoxy, chloro, or methyl. Optionally, $R^2$ is methyl.

A method for the treatment of a protein folding disorder in a subject comprises administering to the subject a compound of the following structure:

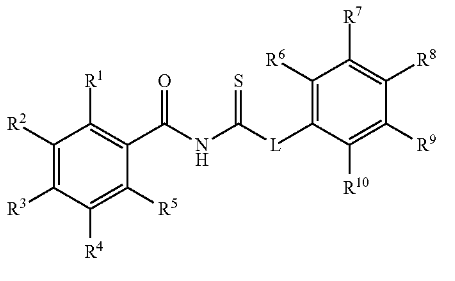

or pharmaceutically acceptable salts or prodrugs thereof. In this class of compounds, L is NH or piperazine; and $R^1$, $R^2$, $R^3$, $R^4$, $R^5$, $R^6$, $R^7$, $R^8$, $R^9$, and $R^{10}$ are each independently selected from hydrogen, halogen, nitro, hydroxyl, substituted or unsubstituted alkoxy, substituted or unsubstituted aryloxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl. Optionally, $R^1$ is hydrogen or fluoro. Optionally, $R^2$ is hydrogen or chloro. Optionally, $R^3$ is hydrogen, methoxy, or benzyloxy. Optionally, $R^7$ is hydrogen or carboxyl. Optionally, $R^8$ is hydrogen, nitro, or substituted or unsubstituted heteroaryl.

A method for the treatment of a protein folding disorder in a subject comprises administering to the subject a compound of the following structure:

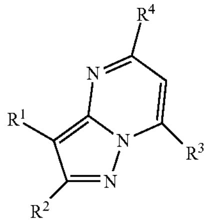

or pharmaceutically acceptable salts or prodrugs thereof. In this class of compounds, $R^1$ is hydrogen or substituted or unsubstituted carbonyl; $R^2$ is hydrogen, carboxyl, or substituted or unsubstituted aryl; $R^3$ is hydrogen, hydroxyl, trifluoromethyl, or substituted or unsubstituted alkyl; and $R^4$ is hydrogen, substituted or unsubstituted alkyl, or substituted or unsubstituted aryl.

A method for the treatment of a protein folding disorder in a subject comprises administering to the subject a compound of the following structure:

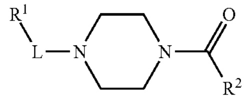

or pharmaceutically acceptable salts or prodrugs thereof. In this class of compounds, L is absent or $-CH_2-$; $R^1$ is substituted or unsubstituted alkyl, substituted or unsubstituted aryl, or substituted or unsubstituted heteroaryl; and $R^2$ is substituted or unsubstituted aryl or substituted or unsubstituted heteroaryl. Optionally, $R^1$ is substituted or unsubstituted phenyl or substituted or unsubstituted quinoline. Optionally, $R^2$ is substituted or unsubstituted phenyl or substituted or unsubstituted furan.

A method for the treatment of a protein folding disorder in a subject comprises administering to the subject a compound of the following structure:

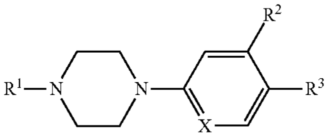

or pharmaceutically acceptable salts or prodrugs thereof. In this class of compounds, $R^1$ is substituted or unsubstituted heterocycloalkenyl or substituted or unsubstituted heteroaryl; $R^2$ and $R^3$ are each independently selected from hydrogen, halogen, trifluoromethyl, or alkoxy; and X is CH or N. Optionally, $R^1$ is substituted or unsubstituted pyrimidinone, substituted or unsubstituted pyrimidine, or substituted or unsubstituted phthalazine. Optionally, $R^2$ is methoxy or trifluoromethyl. Optionally, $R^3$ is chloro or methoxy.

A method for the treatment of a protein folding disorder in a subject comprises administering to the subject a compound of the following structure:

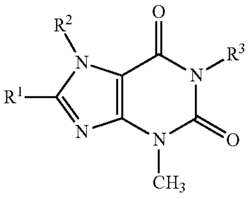

or pharmaceutically acceptable salts or prodrugs thereof. In this class of compounds, $R^1$ is substituted or unsubstituted alkoxy, substituted or unsubstituted aryloxy, substituted or unsubstituted amino, or substituted or unsubstituted piperazine; $R^2$ is hydrogen or substituted or unsubstituted alkyl; and $R^3$ is substituted or unsubstituted alkyl. Optionally, $R^1$ and $R^2$ are combined to form a substituted or unsubstituted heterocycloalkyl or substituted or unsubstituted heterocycloalkenyl.

A method for the treatment of a protein folding disorder in a subject comprises administering to the subject a compound of the following structure:

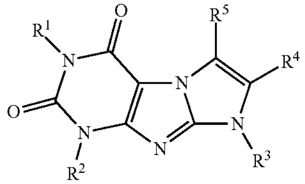

or pharmaceutically acceptable salts or prodrugs thereof. In this class of compounds, $R^1$, $R^2$, $R^3$, and $R^4$ are each independently selected from hydrogen, substituted or unsubstituted alkyl, substituted or unsubstituted alkenyl, substituted or unsubstituted alkynyl, substituted or unsubstituted aryl, or substituted or unsubstituted heteroaryl; and $R^5$ is hydrogen or substituted or unsubstituted alkyl, substituted or unsubstituted alkenyl, or substituted or unsubstituted alkynyl. Optionally, $R^1$ is methyl, ethyl, propyl, allyl, or substituted or unsubstituted benzyl. Optionally, $R^2$ is methyl. Optionally, $R^3$ is methyl, propyl, butyl, isobutyl, allyl, substituted or unsubstituted phenyl, or substituted or unsubstituted benzyl. Optionally, $R^4$ is methyl. Optionally, $R^5$ is hydrogen or methyl.

A method for the treatment of a protein folding disorder in a subject comprises administering to the subject a compound of the following structure:

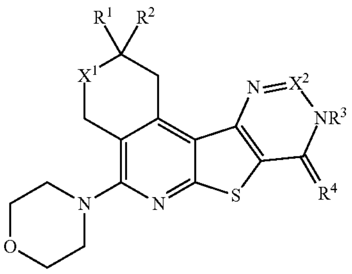

or pharmaceutically acceptable salts or prodrugs thereof. In this class of compounds, $R^1$ and $R^2$ are each independently selected from hydrogen and substituted or unsubstituted alkyl; $R^3$ is hydrogen, substituted or unsubstituted alkyl, or substituted or unsubstituted alkenyl; $R^4$ is O or $NR^5$, wherein $R^5$ is substituted or unsubstituted amino or substituted or unsubstituted alkyl; $X^1$ is $CH_2$, O, or NH; and $X^2$ is CH or N. Optionally, $X^1$ is O or $CH_2$. Optionally, $R^1$ and $R^2$ are hydrogen or methyl. Optionally, $R^3$ and $R^4$ are combined to form a substituted or unsubstituted heterocycloalkyl or substituted or unsubstituted heterocycloalkenyl.

A method for the treatment of a protein folding disorder in a subject comprises administering to the subject a compound of the following structure:

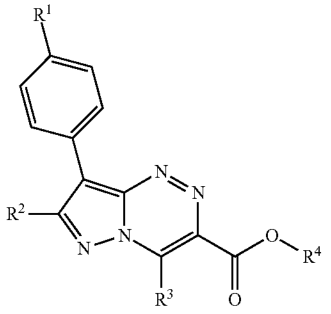

or pharmaceutically acceptable salts or prodrugs thereof. In this class of compounds, $R^1$ is hydrogen, halogen, alkoxy, substituted or unsubstituted amino, or substituted or unsubstituted alkyl; and $R^2$, $R^3$, and $R^4$ are each independently substituted or unsubstituted alkyl. Optionally, $R^1$ is chloro, fluoro, or methoxy. Optionally, $R^2$ is methyl. Optionally, $R^3$ is methyl. Optionally, $R^4$ is methyl or ethyl.

Additional or alternative compounds that can be administered to a subject for treating protein folding disorders (e.g., cystic fibrosis) are also provided. The compounds include the following:

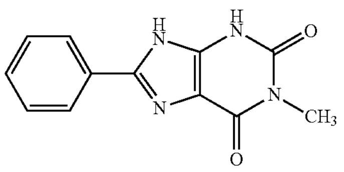

-continued

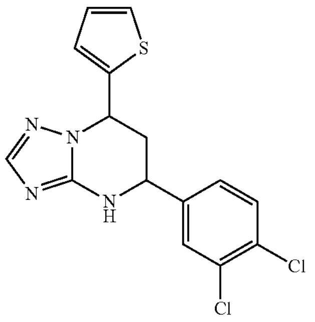

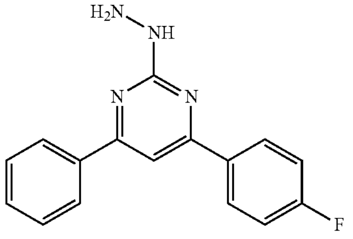

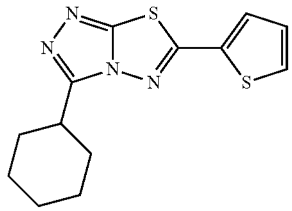

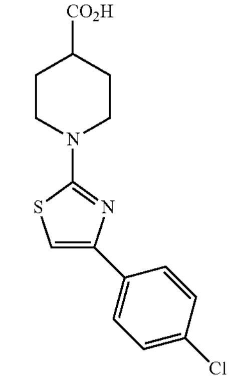

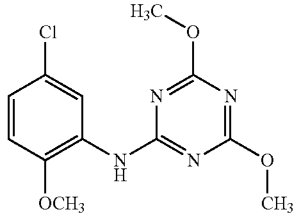

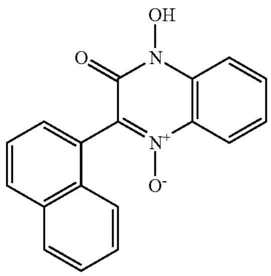

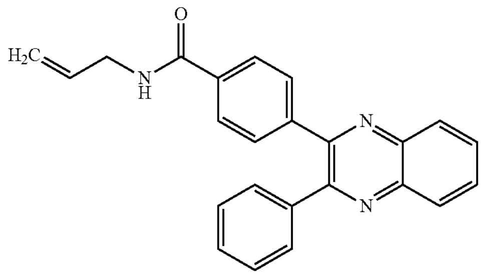

-continued
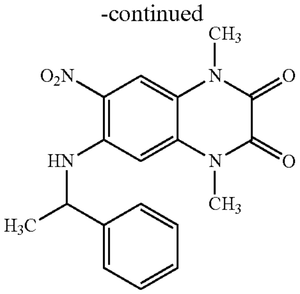
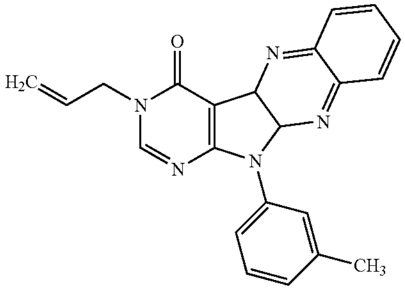
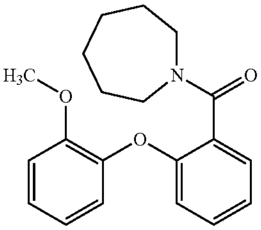
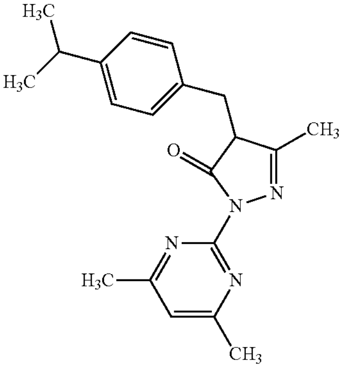
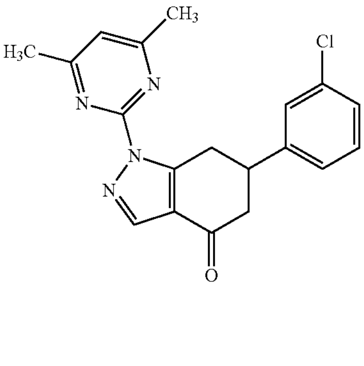
-continued
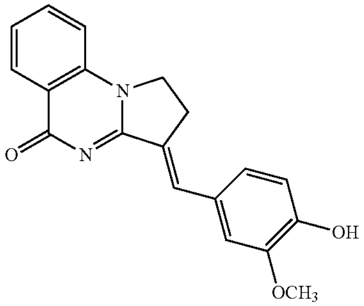
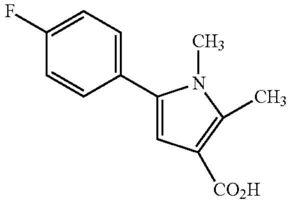
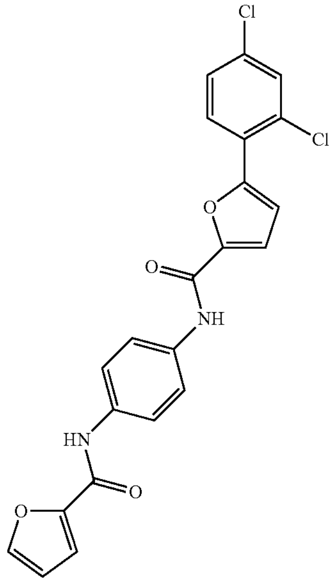
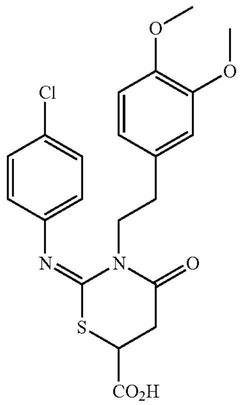
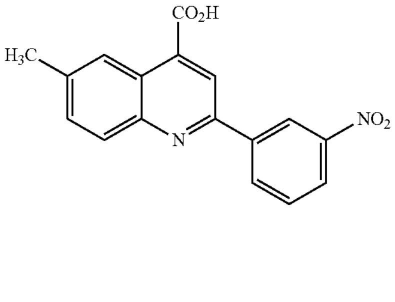

-continued

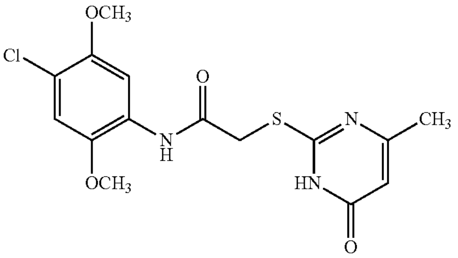

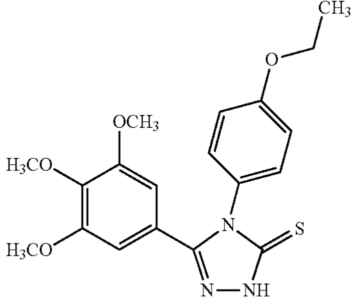

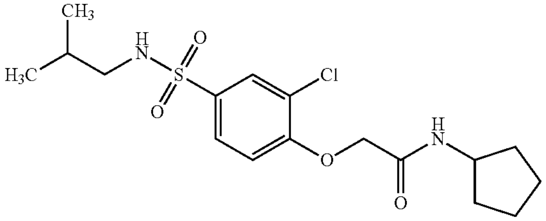

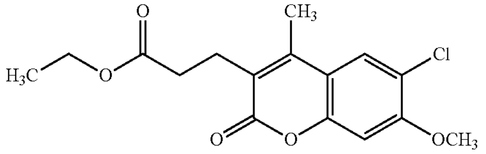

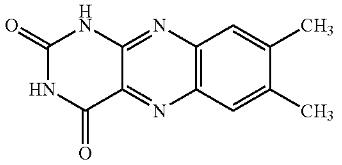

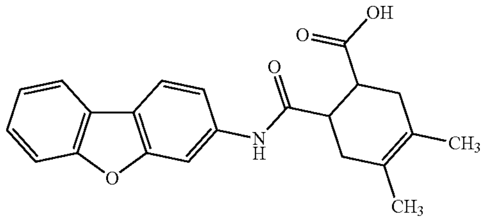

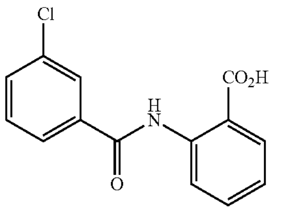

-continued

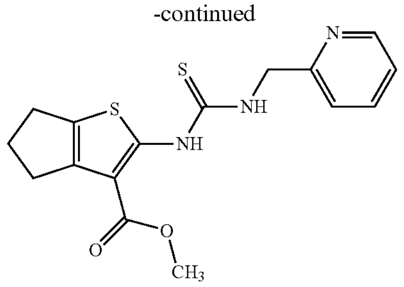

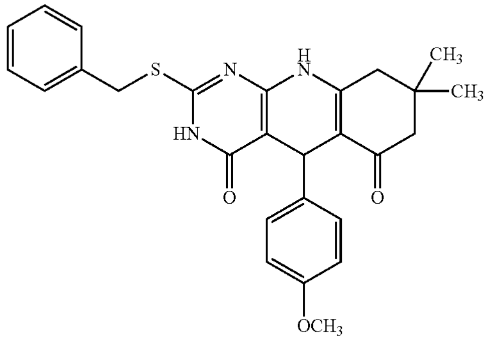

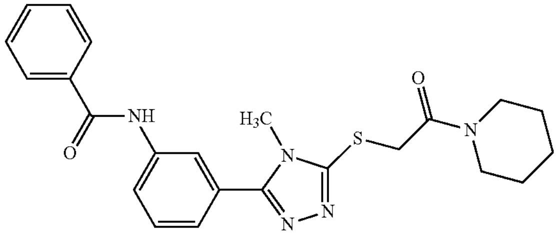

or pharmaceutically acceptable salts and prodrugs thereof. Optionally, the method can further include the step of selecting a subject with cystic fibrosis.

A method of screening for a compound for treating a protein folding disorder (e.g., cystic fibrosis) is also provided. The method includes contacting a cell that endogenously expresses a CFTR mutation with the compound to be screened, and then detecting a rescue of halide efflux from the cell (e.g., using an SPQ assay). The halide efflux rescue indicates that the compound is useful in treating cystic fibrosis. The cell can be, for example, a CF human lung and/or airway epithelial cell. Optionally, the cell is comprised of the CFBE41o-cell line. Optionally, the cell does not overexpress the CFTR mutation. Optionally, the CFTR mutation is delF508-CFTR. Optionally, the halide efflux is chloride efflux. The method of screening can further comprise performing the method with multiple doses of the compound. Optionally, the method of screening can further comprise determining CFTR glycosylation or CFTR immunoprecipitation.

DETAILED DESCRIPTION

Figure 1:
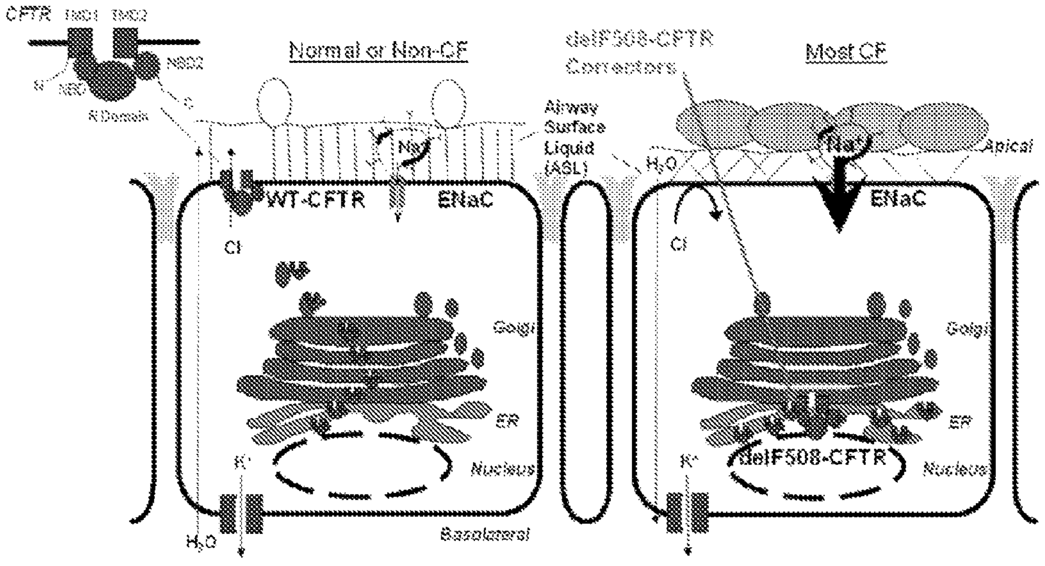
FIG. 1 is a schematic showing a general approach for identifying delF508-CFTR correctors.

The compounds and methods described herein are useful in the treatment of protein folding disorders. The compounds and methods described herein can be useful, for example, in the treatment of cystic fibrosis, familial hypercholesterolemia, diabetes mellitus, alpha1 antitrypsin deficiency, Fabry's disease, Gaucher's disease, Pompe's disease, hypothyrosis, and Alzheimer's disease. For example, described herein are compounds and methods useful in the treatment of cystic fibrosis. These compounds are able to correct the misfolding or defective trafficking of delF508-CFTR; thus, the compounds are effective as CFTR correctors (i.e., the compounds are effective in rescuing halide efflux in a cell). Methods for screening for CFTR corrector compounds are also described herein.

A class of CFTR correctors described herein is represented by Formula I:

I

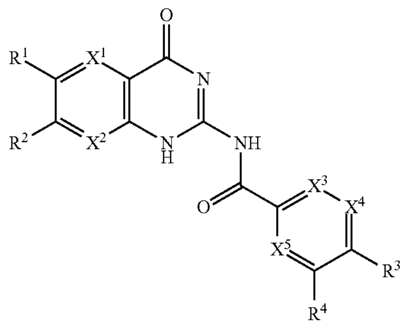

and pharmaceutically acceptable salts or prodrugs thereof.

In Formula I, $R^1$, $R^2$, $R^3$, and $R^4$ are each independently selected from hydrogen, halogen, nitro, hydroxyl, substituted or unsubstituted alkoxy, substituted or unsubstituted aryloxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl. In some examples, $R^3$ is chloro.

In some examples of Formula I, $R^1$ and $R^2$ are each independently selected from substituted or unsubstituted alkoxy and substituted or unsubstituted aryloxy. For example, $R^1$ and $R^2$ are optionally methoxy.

Additionally in Formula I, $X^1$, $X^2$, $X^3$, $X^4$, and $X^5$ are each independently selected from CH and N. In some examples, $X^1$, $X^2$, $X^3$, $X^4$, and $X^5$ are CH.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{26}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. For example, substituted alkyl groups can include fluorinated alkyl groups such as 1-fluoromethyl or trifluoromethyl. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane ($-(CH_2)_9-CH_3$).

In some examples of Formula I, if $X^1$, $X^2$, $X^3$, $X^4$, and $X^5$ are each CH, $R^1$ and $R^2$ are methoxy, and $R^4$ is hydrogen, then $R^3$ is not hydrogen or chloro.

In some examples, Formula I is represented by Structure I-A:

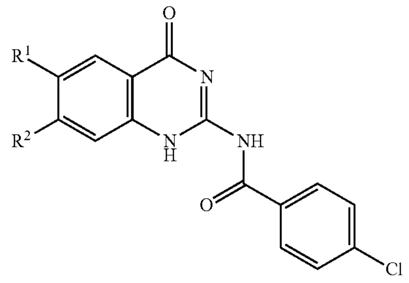

In Structure I-A, $R^1$ and $R^2$ are substituted or unsubstituted alkoxy or aryloxy groups. In some examples, $R^1$ and $R^2$ are not simultaneously methoxy.

In some examples, Formula I is represented by Structure I-B:

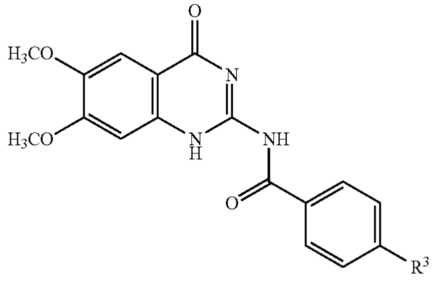

In Structure I-B, $R^3$ is as defined above for Formula I. In some examples, $R^3$ is not hydrogen.

In some examples, Formula I is represented by Structure I-C:

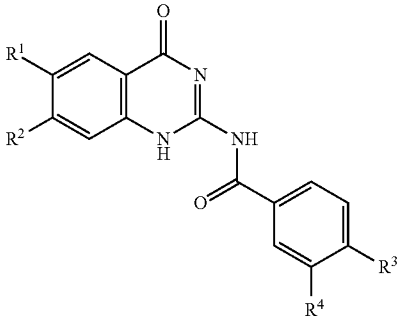

In Structure I-C, $R^1$ and $R^2$ are substituted or unsubstituted alkoxy or aryloxy groups and $R^3$ and $R^4$ are as defined above for Formula I. In some examples, when $R^3$ is chloro and $R^4$ is hydrogen, then $R^1$ and $R^2$ are not simultaneously methoxy.

In some examples, Formula I is represented by Structure I-D:

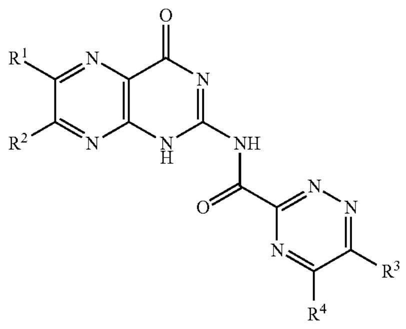

In Structure I-D, $R^1$, $R^2$, $R^3$, and $R^4$ are as defined above for Formula I.

In some examples, Formula I is represented by Structure I-E:

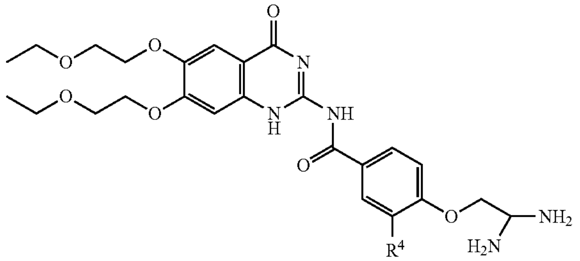

In Structure I-E, $R^4$ is as defined above for Formula I.

Examples of Formula I include the following compounds:

Compound I-1

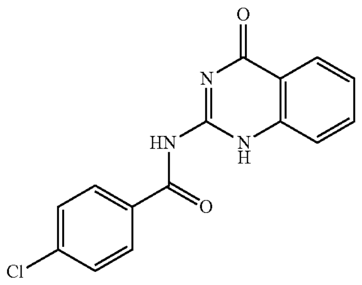

Compound I-2

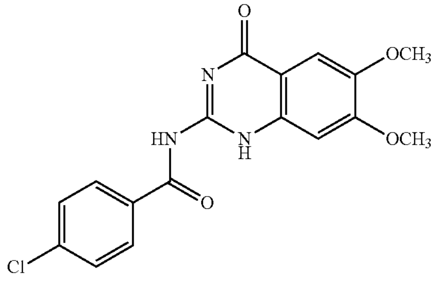

-continued

Compound I-3

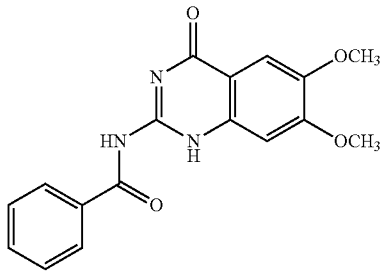

Compound I-4

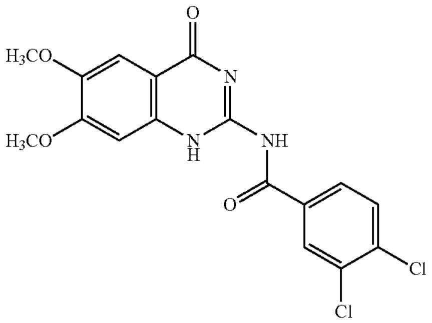

In some examples of Formula I, the compound is not Compound I-1, Compound I-2, or Compound I-3.

A class of CFTR correctors described herein is represented by Formula II:

II

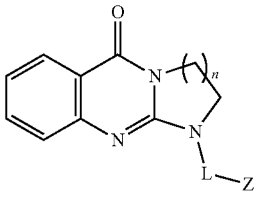

and pharmaceutically acceptable salts or prodrugs thereof.

In Formula II, L is $—CH_2—$, $—CH_2—CH_2—$, C═O, or absent. Optionally, L is $—CH_2—$ or $—CH_2—CH_2—$.

Also, in Formula II, n is 1 or 2.

Additionally, in Formula II, Z is hydrogen, methyl, or substituted or unsubstituted aryl. Optionally, Z is substituted or unsubstituted aryl.

In some examples, Formula II is represented by Structure II-A or Structure II-B:

Structure II-A

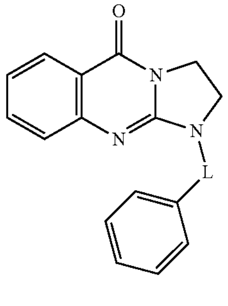

-continued
Structure II-B
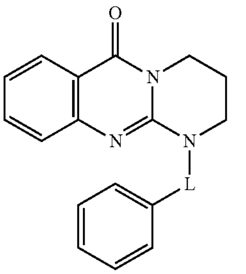
In Structures II-A and II-B, L is as defined above for Formula II.
Examples of Formula II include the following compounds:
Compound II-1
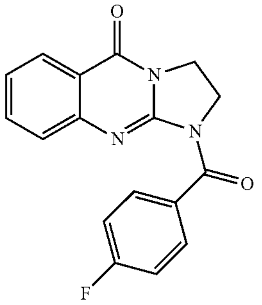
Compound II-2
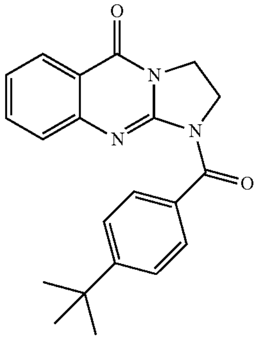
Compound II-3
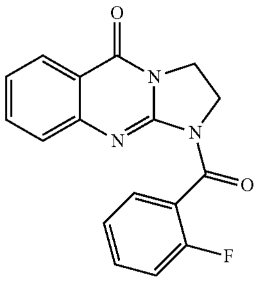
-continued
Compound II-4
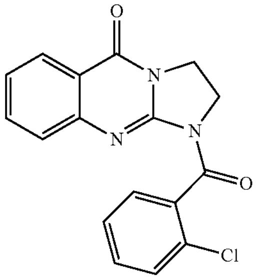
Compound II-5
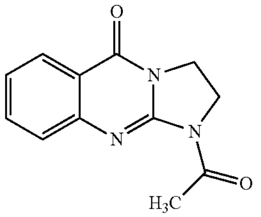
Compound II-6
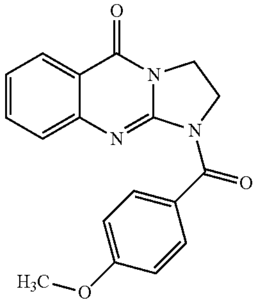
Compound II-7
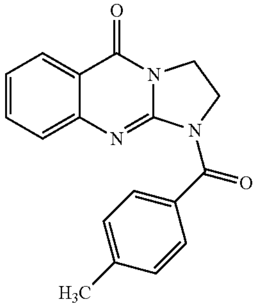
Compound II-8
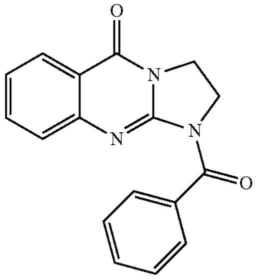

-continued
Compound II-9
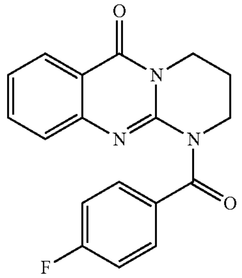
Compound II-10
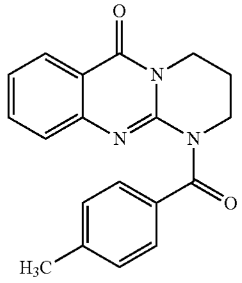
Compound II-11
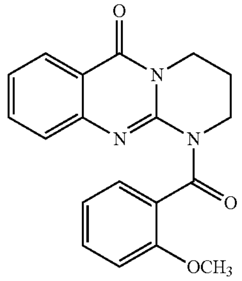
Compound II-12
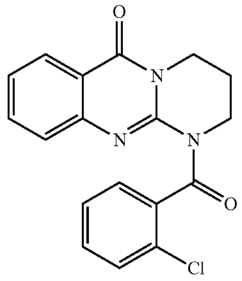
Compound II-13
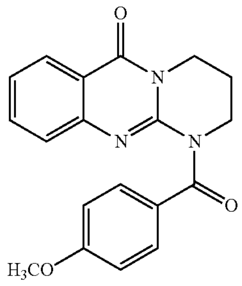
-continued
Compound II-14
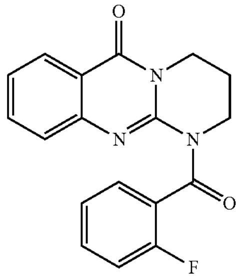
Compound II-15
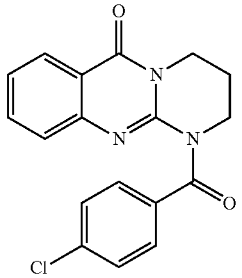
Compound II-16
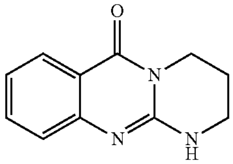
Compound II-17
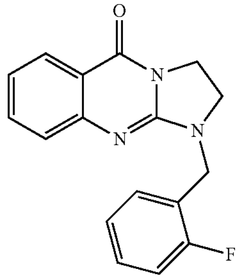
Compound II-18
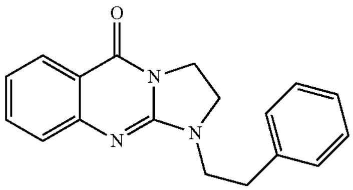
Compound II-19
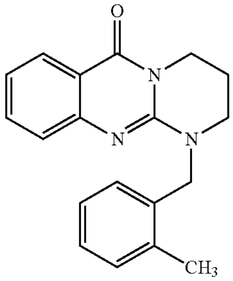

-continued

Compound II-20

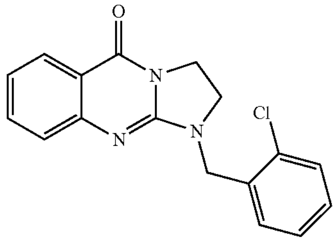

Compound II-21

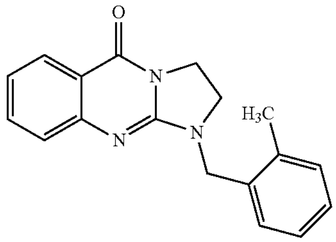

Compound II-22

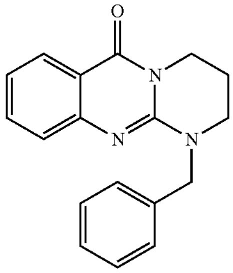

Compound II-23

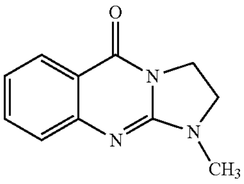

A class of CFTR correctors described herein is represented by Formula III:

III

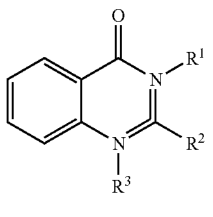

and pharmaceutically acceptable salts or prodrugs thereof.

In Formula III, $R^1$ and $R^3$ are independently absent or each independently selected from hydrogen or substituted or unsubstituted alkyl.

Also, in Formula III, $R^2$ is substituted or unsubstituted amino, substituted or unsubstituted thio, or substituted or unsubstituted heterocycloalkyl.

Additionally, in Formula III, ⎓ is a single bond or double bond, wherein two double bonds are not adjacent.

In some examples of Formula III, $R^1$ and $R^2$ are combined to form a substituted or unsubstituted aryl or substituted or unsubstituted heteroaryl. For example, $R^1$ can be a substituted ethylene group and $R^2$ can be a substituted ethenamine group that combine to form a substituted pyrimidine group.

Examples of Formula III include the following compounds:

Compound III-1

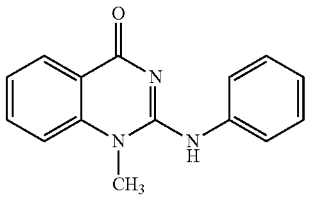

Compound III-2

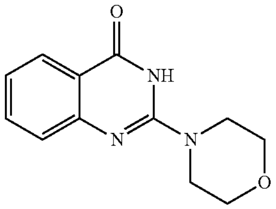

Compound III-3

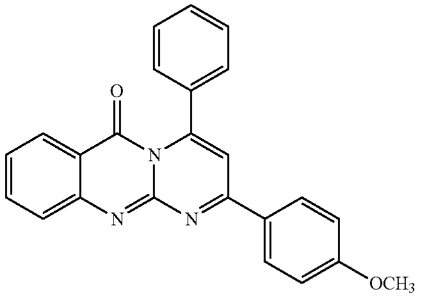

Compound III-4

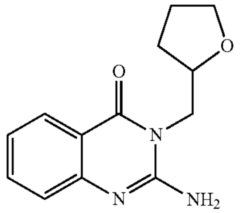

Compound III-5

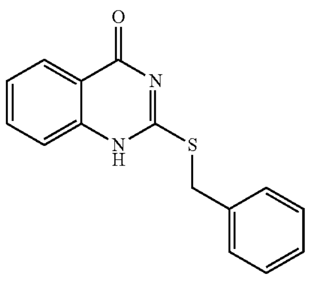

A class of CFTR correctors described herein is represented by Formula IV:

IV

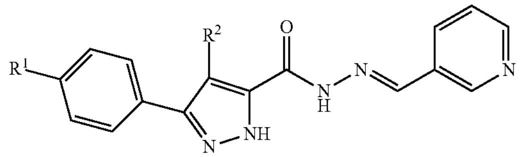

and pharmaceutically acceptable salts and prodrugs thereof.

In Formula IV, $R^1$ is hydrogen, halogen, alkoxy, or substituted or unsubstituted alkyl. Optionally, $R^1$ is ethoxy, chloro, or methyl.

Also, in Formula IV, $R^2$ is hydrogen or substituted or unsubstituted alkyl. Optionally, $R^2$ is methyl.

Examples of Formula IV include the following compounds:

Compound IV-1

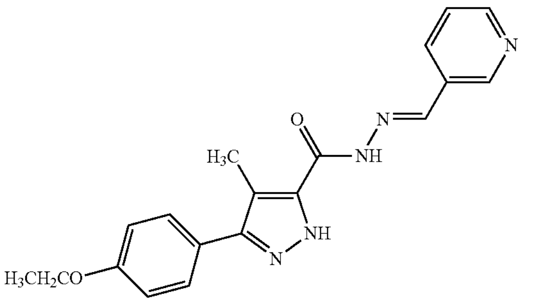

Compound IV-2

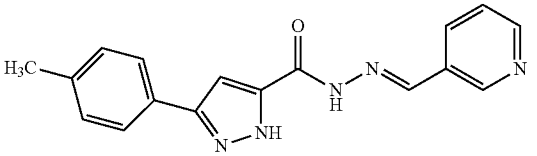

Compound IV-3

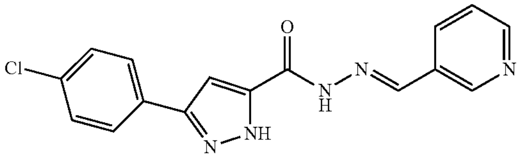

A class of CFTR correctors described herein is represented by Formula V:

V

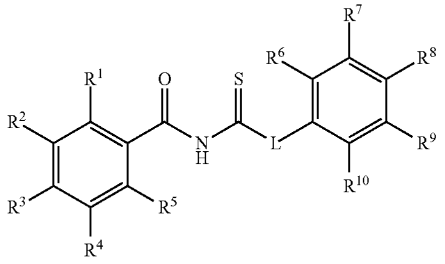

and pharmaceutically acceptable salts or prodrugs thereof.

In Formula V, L is NH or piperazine.

Also, in Formula V, $R^1$, $R^2$, $R^3$, $R^4$, $R^5$, $R^6$, $R^7$, $R^8$, $R^9$, and $R^{10}$ are each independently selected from hydrogen, halogen, nitro, hydroxyl, substituted or unsubstituted alkoxy, substituted or unsubstituted aryloxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl. In some examples, $R^1$ is hydrogen or fluoro. In some examples, $R^2$ is hydrogen or chloro. In some examples, $R^3$ is hydrogen, methoxy, or benzyloxy. In some examples, $R^7$ is hydrogen or carboxyl. In some examples, $R^8$ is hydrogen, nitro, or substituted or unsubstituted heteroaryl.

Examples of Formula V include the following compounds:

Compound V-1

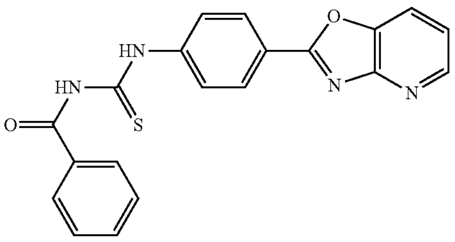

Compound V-2

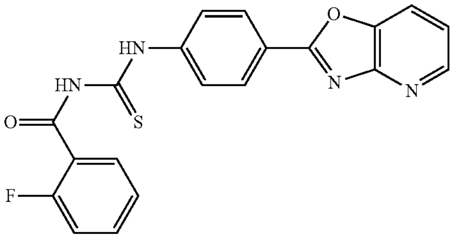

Compound V-3

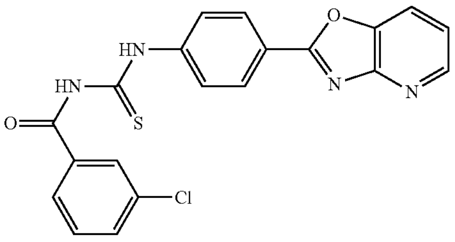

Compound V-4

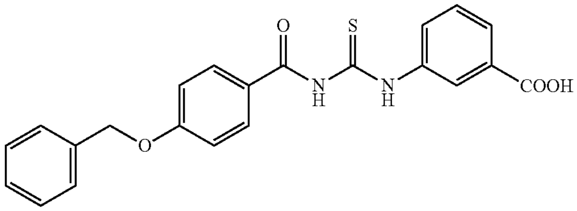

-continued

Compound V-5

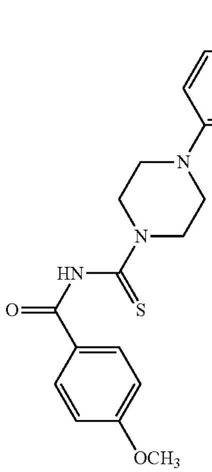

A class of CFTR correctors described herein is represented by Formula VI:

VI

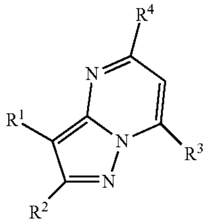

and pharmaceutically acceptable salts or prodrugs thereof.

In Formula VI, $R^1$ is hydrogen or substituted or unsubstituted carbonyl.

Also, in Formula VI, $R^2$ is hydrogen, carboxyl, or substituted or unsubstituted aryl.

Additionally, in Formula VI, $R^3$ is hydrogen, hydroxyl, trifluoromethyl, or substituted or unsubstituted alkyl.

Further, in Formula VI, $R^4$ is hydrogen, substituted or unsubstituted alkyl, or substituted or unsubstituted aryl.

Examples of Formula VI include the following compounds:

Compound VI-1

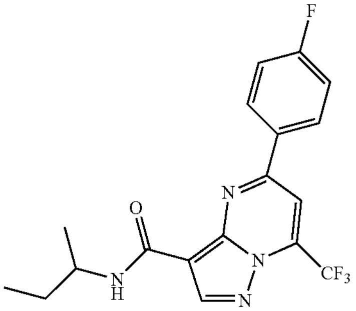

-continued

Compound VI-2

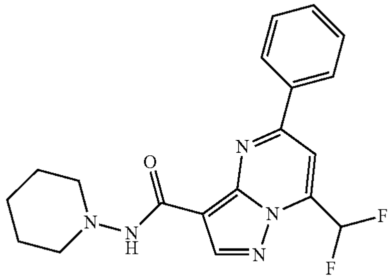

Compound VI-3

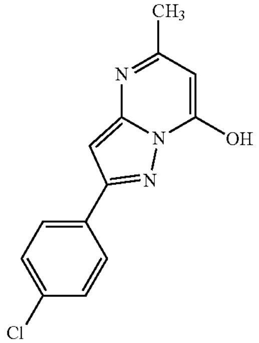

Compound VI-4

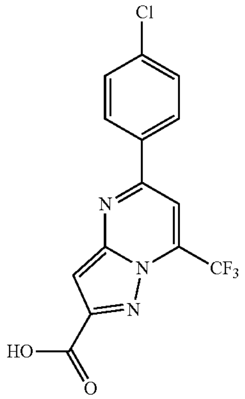

A class of CFTR correctors described herein is represented by Formula VII:

VII

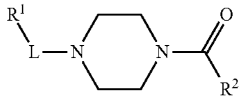

and pharmaceutically acceptable salts or prodrugs thereof.

In Formula VII, L is absent or $-CH_2-$.

Also, in Formula VII, $R^1$ is substituted or unsubstituted alkyl, substituted or unsubstituted aryl, or substituted or unsubstituted heteroaryl. Optionally, $R^1$ is substituted or unsubstituted phenyl or substituted or unsubstituted quinoline.

Additionally, in Formula VII, $R^2$ is substituted or unsubstituted aryl or substituted or unsubstituted heteroaryl. Optionally, $R^2$ is substituted or unsubstituted phenyl or substituted or unsubstituted furan.

Examples of Formula VII include the following compounds:

Compound VII-1

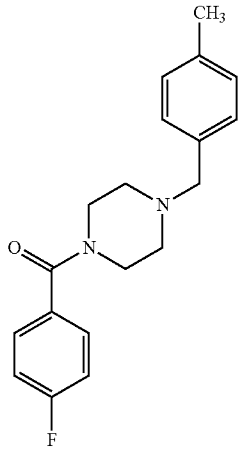

Compound VII-2

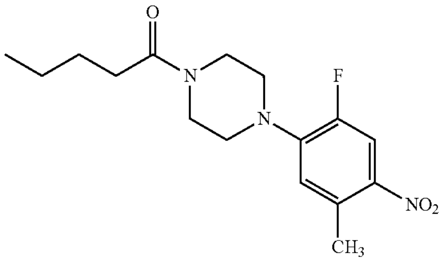

Compound VII-3

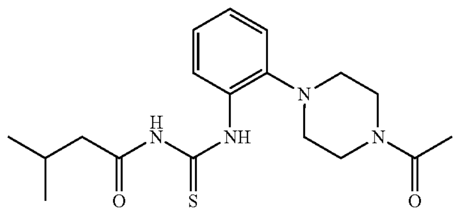

Compound VII-4

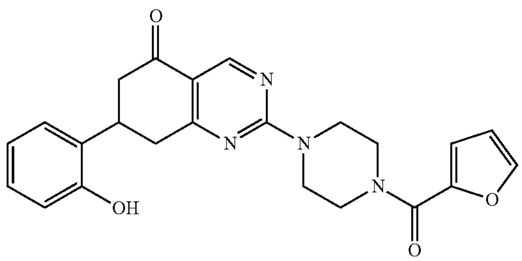

-continued

Compound VII-5

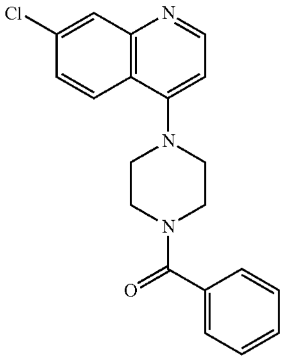

Compound VII-6

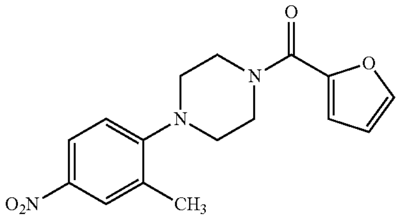

A class of CFTR correctors described herein is represented by Formula VIII:

VIII

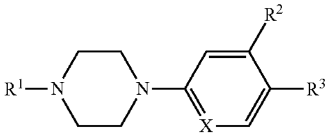

and pharmaceutically acceptable salts or prodrugs thereof.

In Formula VIII, $R^1$ is substituted or unsubstituted heterocycloalkenyl or substituted or unsubstituted heteroaryl. Optionally, $R^1$ is substituted or unsubstituted pyrimidinone, substituted or unsubstituted pyrimidine, or substituted or unsubstituted phthalazine.

Also, in Formula VIII, $R^2$ and $R^3$ are each independently selected from hydrogen, halogen, trifluoromethyl, or alkoxy. Optionally, $R^2$ is methoxy or trifluoromethyl. Optionally, $R^3$ is chloro or methoxy.

Additionally, in Formula VIII, X is CH or N.

Examples of Formula VIII include the following compounds:

Compound VIII-1

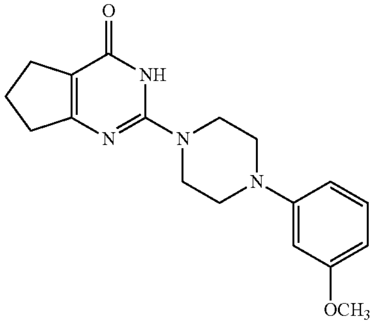

-continued

Compound VIII-2

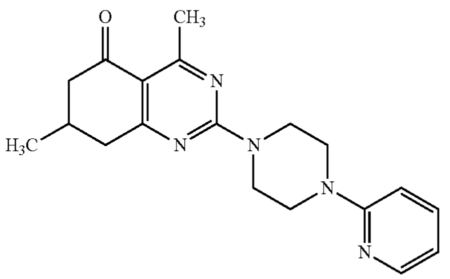

Compound VIII-3

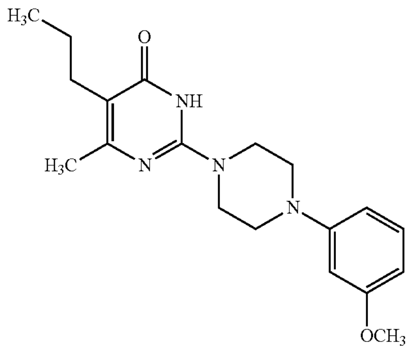

Compound VIII-4

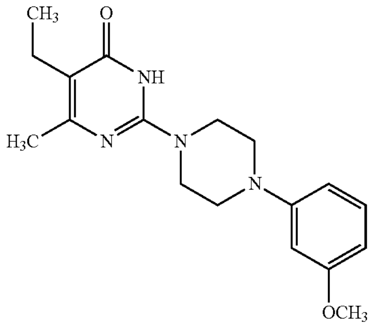

Compound VIII-5

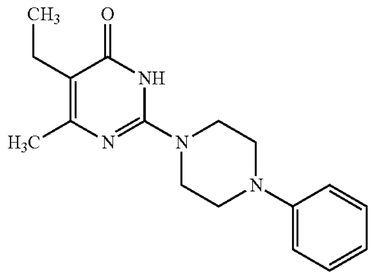

Compound VIII-6

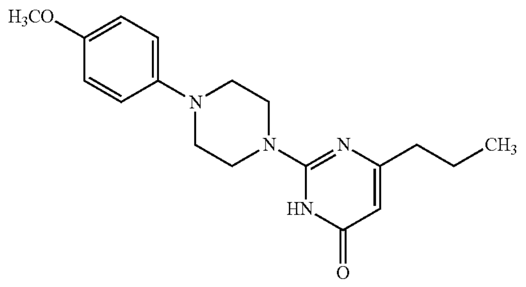

-continued

Compound VIII-7

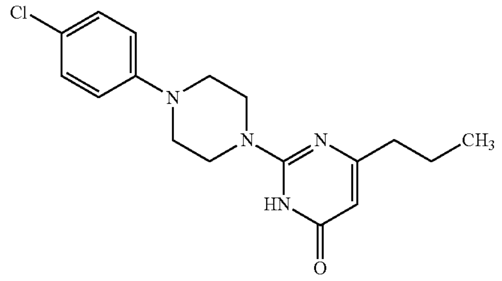

Compound VIII-8

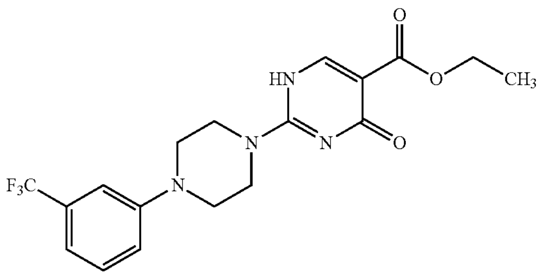

Compound VIII-9

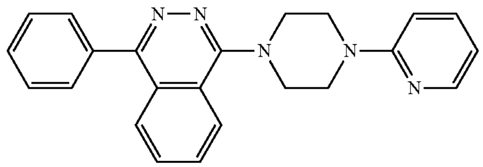

Compound VIII-10

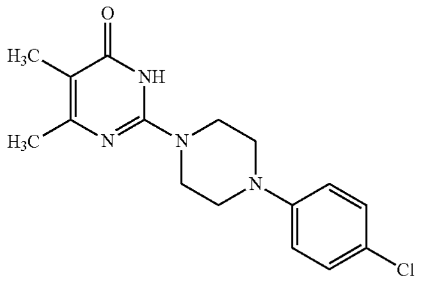

A class of CFTR correctors described herein is represented by Formula IX:

IX

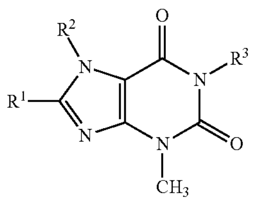

and pharmaceutically acceptable salts or prodrugs thereof.

In Formula IX, $R^1$ is substituted or unsubstituted alkoxy, substituted or unsubstituted aryloxy, substituted or unsubstituted amino, or substituted or unsubstituted piperazine.

Also, in Formula IX, $R^2$ is hydrogen or substituted or unsubstituted alkyl.

Additionally, in Formula IX, $R^3$ is substituted or unsubstituted alkyl.

In some examples, $R^1$ and $R^2$ are combined to form a substituted or unsubstituted heterocycloalkyl or substituted or unsubstituted heterocycloalkenyl.

Examples of Formula IX include the following compounds:

Compound IX-1

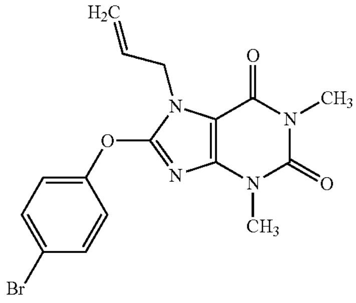

Compound IX-2

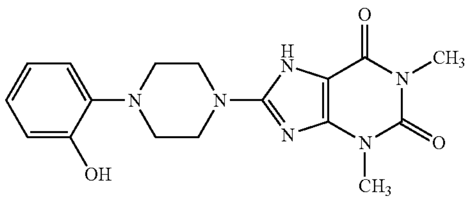

Compound IX-3

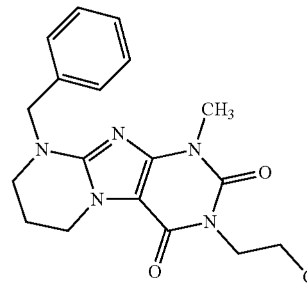

A class of CFTR correctors described herein is represented by Formula X:

X

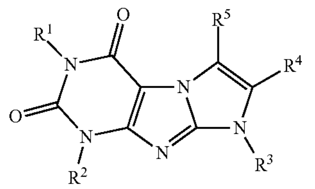

and pharmaceutically acceptable salt or prodrug thereof.

In Formula X, $R^1$, $R^2$, $R^3$, and $R^4$ are each independently selected from hydrogen, substituted or unsubstituted alkyl, substituted or unsubstituted alkenyl, substituted or unsubstituted alkynyl, substituted or unsubstituted aryl, or substituted or unsubstituted heteroaryl. Optionally, $R^1$ is methyl, ethyl, propyl, allyl, or substituted or unsubstituted benzyl. Optionally, $R^2$ is methyl. Optionally, $R^3$ is methyl, propyl, butyl, isobutyl, allyl, substituted or unsubstituted phenyl, or substituted or unsubstituted benzyl. Optionally, $R^4$ is methyl.

Also, in Formula X, $R^5$ is hydrogen or substituted or unsubstituted alkyl, substituted or unsubstituted alkenyl, or substituted or unsubstituted alkynyl. Optionally, $R^5$ is hydrogen or methyl.

Examples of Formula X include the following compounds:

Compound X-1

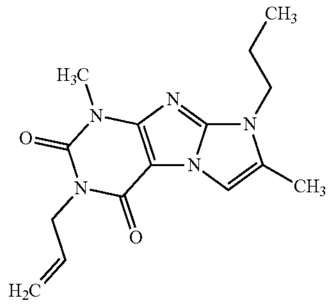

Compound X-2

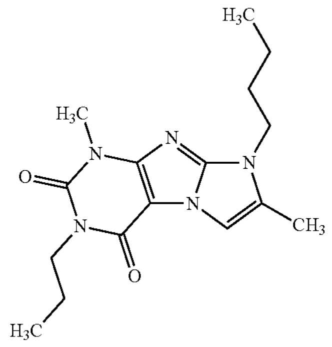

Compound X-3

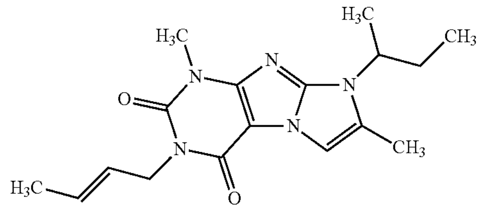

Compound X-4

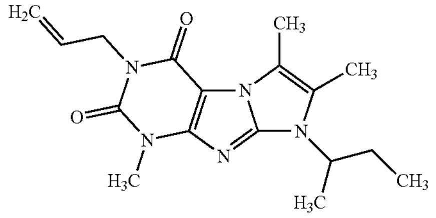

Compound X-5

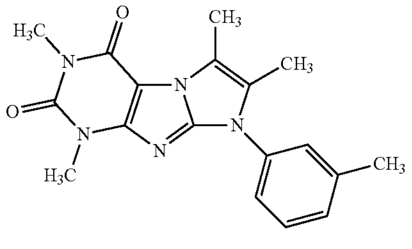

-continued
Compound X-6
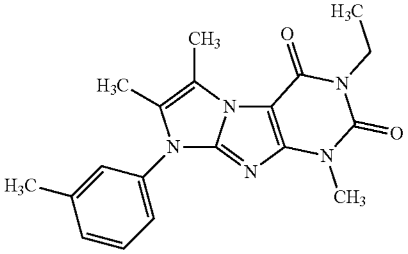
Compound X-7
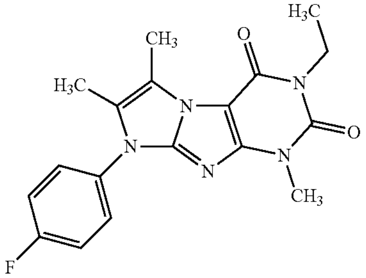
Compound X-8
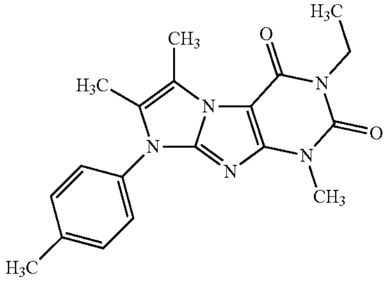
Compound X-9
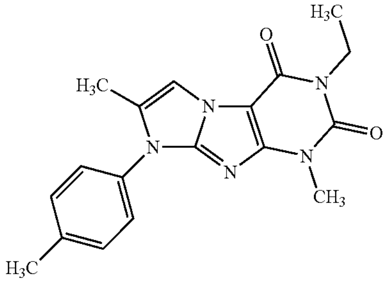
Compound X-10
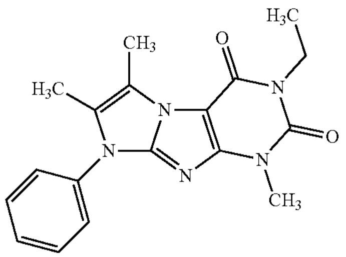
-continued
Compound X-11
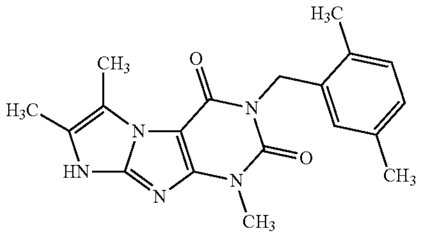
Compound X-12
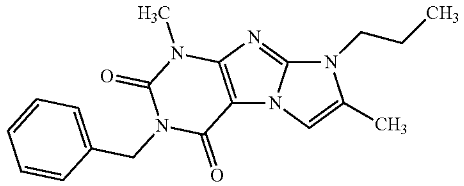
Compound X-13
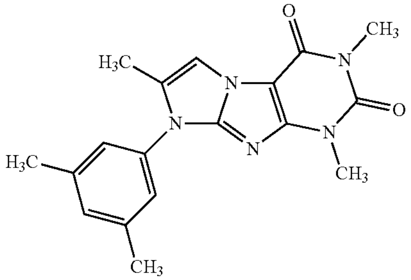
Compound X-14
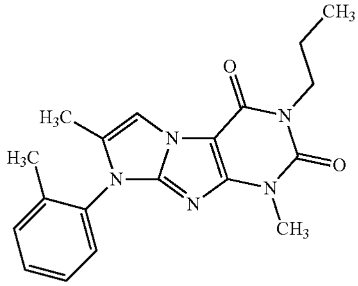
Compound X-15
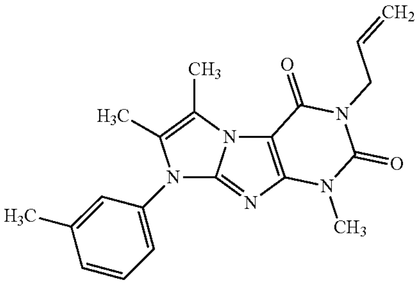

-continued
Compound X-16
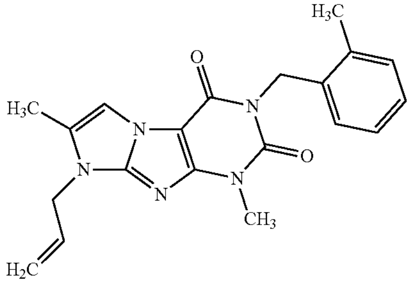
Compound X-17
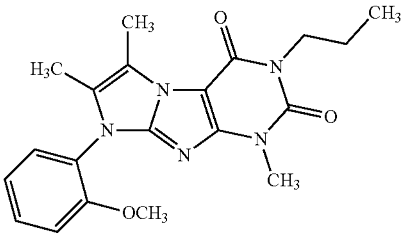
Compound X-18
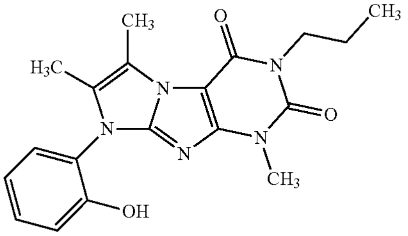
Compound X-19
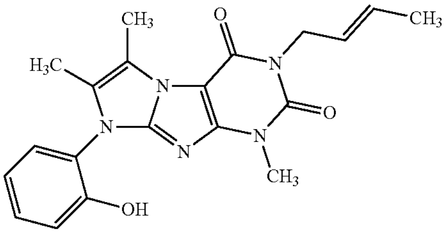
Compound X-20
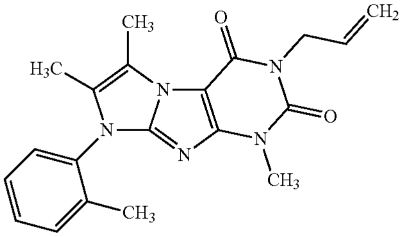
Compound X-21
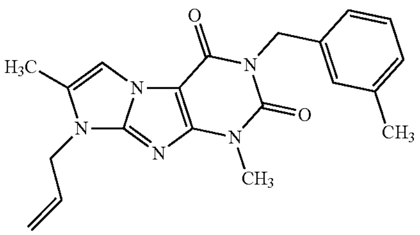
-continued
Compound X-22
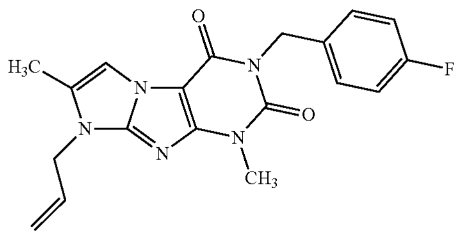
Compound X-23
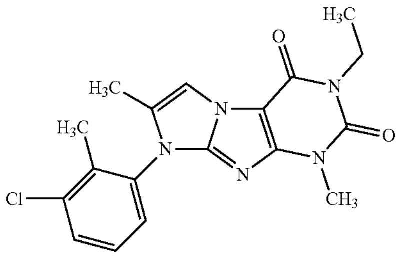
Compound X-24
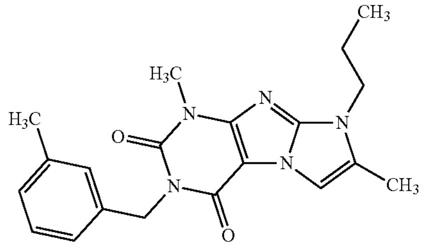
Compound X-25
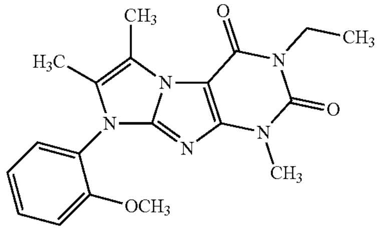
Compound X-26
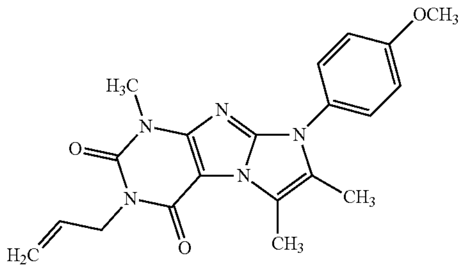
A class of CFTR correctors described herein is represented by Formula XI:

XI

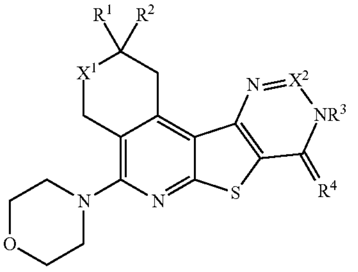

and pharmaceutically acceptable salts or prodrugs thereof.

In Formula XI, $R^1$ and $R^2$ are each independently selected from hydrogen and substituted or unsubstituted alkyl. Optionally, $R^1$ and $R^2$ are hydrogen or methyl.

Also, in Formula XI, $R^3$ is hydrogen, substituted or unsubstituted alkyl, or substituted or unsubstituted alkenyl.

Additionally, in Formula XI, $R^4$ is O or $NR^5$, wherein $R^5$ is substituted or unsubstituted amino or substituted or unsubstituted alkyl.

Also, in Formula XI, $X^1$ is $CH_2$, O, or NH.

Further, in Formula XI, $X^2$ is CH or N.

In some examples of Formula XI, $R^3$ and $R^4$ are combined to form a substituted or unsubstituted heterocycloalkyl or substituted or unsubstituted heterocycloalkenyl.

Examples of Formula XI include the following compounds:

Compound XI-1

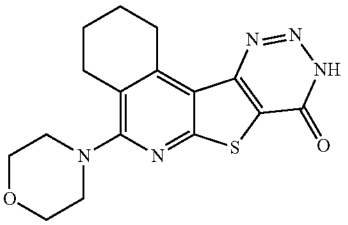

Compound XI-2

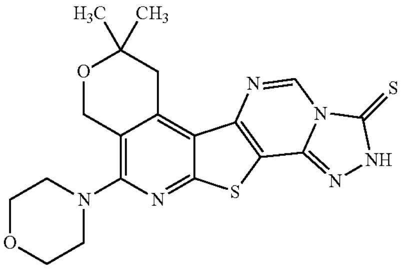

A class of CFTR correctors described herein is represented by Formula XII:

XII

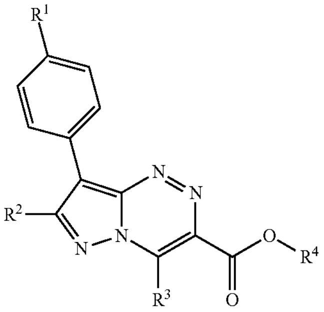

and pharmaceutically acceptable salts or prodrugs thereof.

In Formula XII, $R^1$ is hydrogen, halogen, alkoxy, substituted or unsubstituted amino, or substituted or unsubstituted alkyl. Optionally, $R^1$ is chloro, fluoro, or methoxy.

Also, in Formula XII, $R^2$, $R^3$, and $R^4$ are each independently substituted or unsubstituted alkyl. Optionally, $R^2$ is methyl. Optionally, $R^3$ is methyl. Optionally, $R^4$ is methyl or ethyl.

Examples of Formula XII include the following compounds:

Compound XII-1

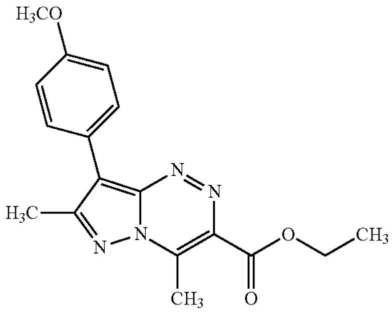 [SMILES: CCOC(=O)c1nnc2c(-c3ccc(OC)cc3)c(C)nn2c1C]

Compound XII-2

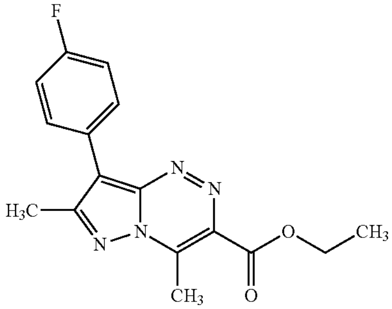

Compound XII-3

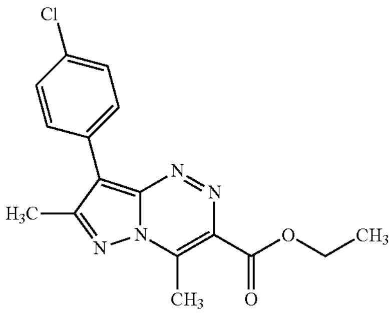 [SMILES: CCOC(=O)c1nnc2c(-c3ccc(Cl)cc3)c(C)nn2c1C]

-continued
Compound XII-4
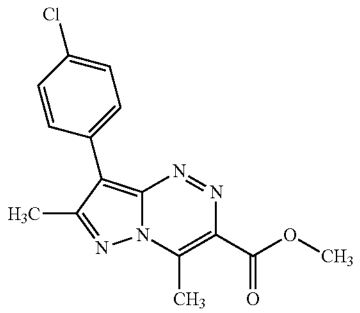 [SMILES: COC(=O)c1nnc2c(-c3ccc(Cl)cc3)c(C)nn2c1C]
Additional compounds useful with the methods described herein include the following Compounds 1-28:
Compound 1
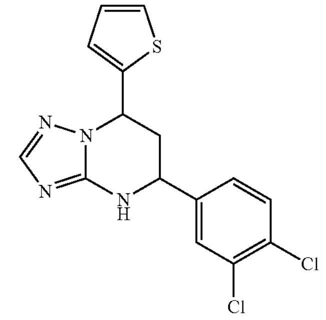
Compound 2
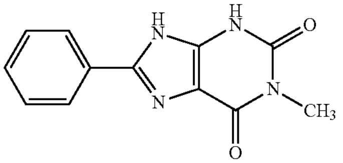
Compound 3
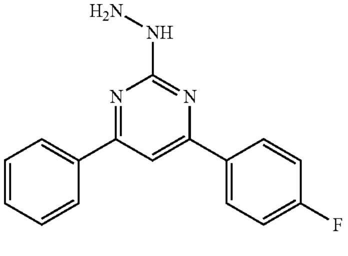
Compound 4
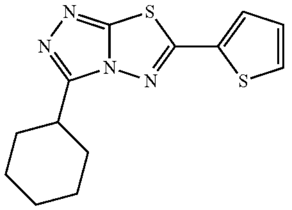
-continued
Compound 5
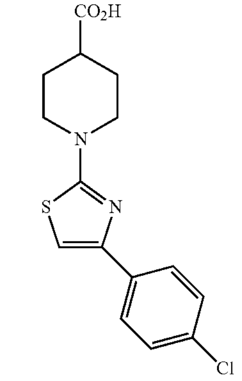
Compound 6
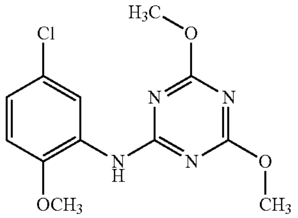
Compound 7
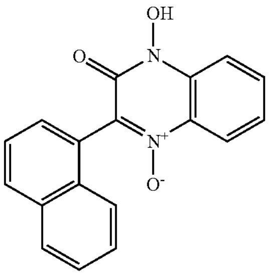
Compound 8
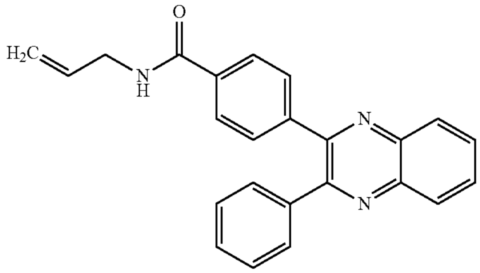
Compound 9
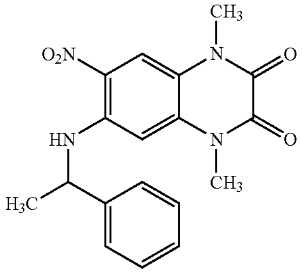

-continued
Compound 10
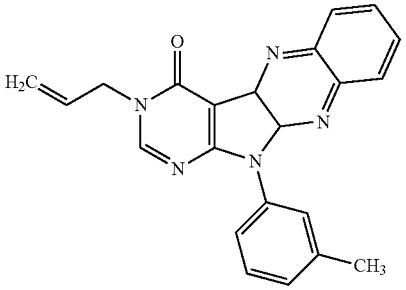
Compound 11
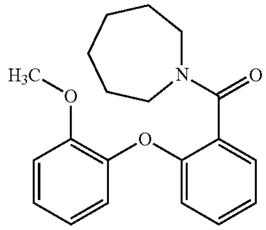
Compound 12
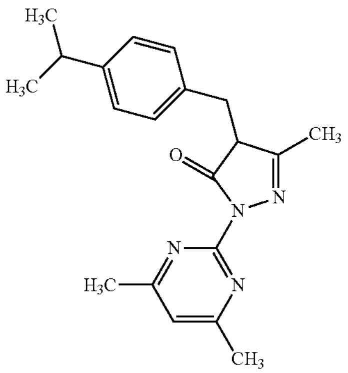
Compound 13
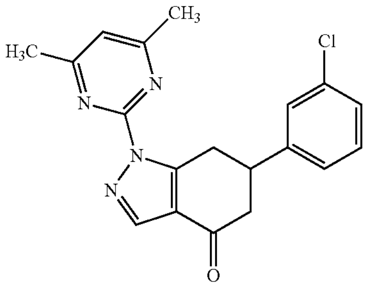
Compound 14
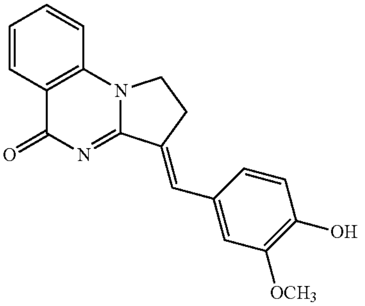
-continued
Compound 15
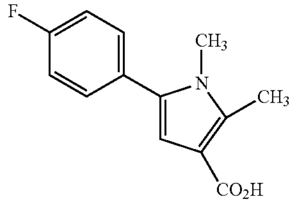
Compound 16
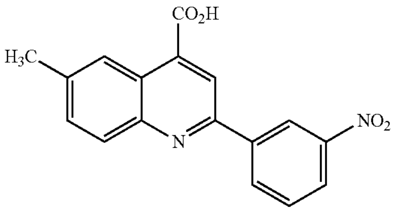
Compound 17
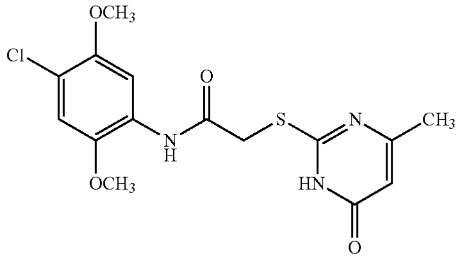
Compound 18
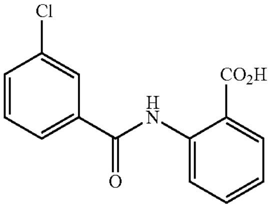
Compound 19
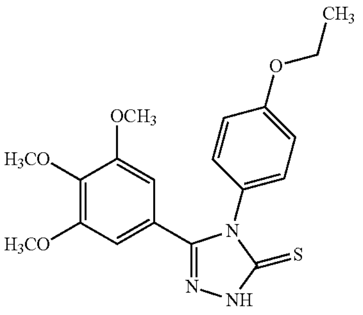
Compound 20
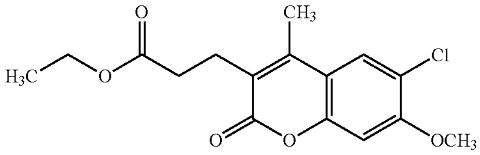

-continued

Compound 21

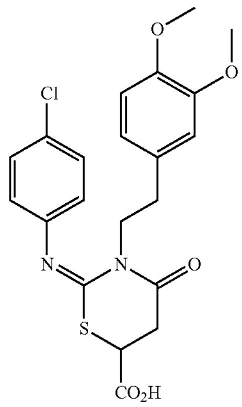

Compound 22

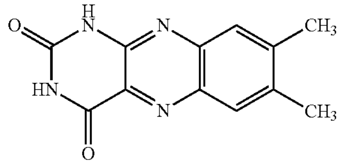

Compound 23

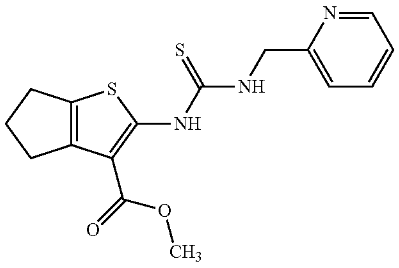

Compound 24

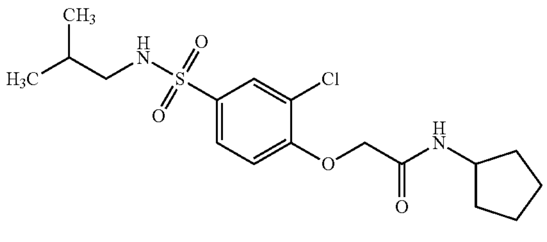

Compound 25

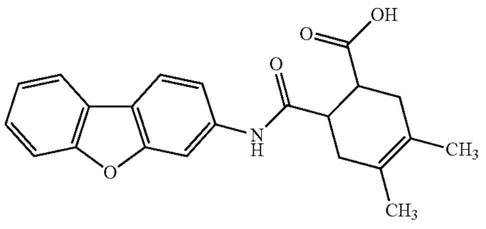

-continued

Compound 26

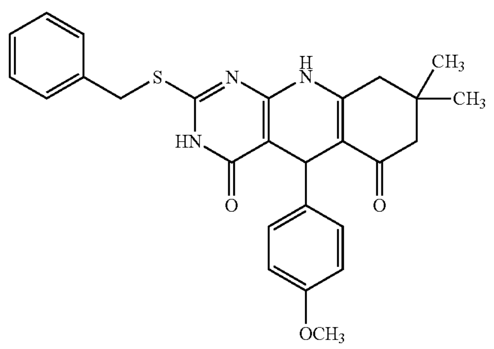

Compound 27

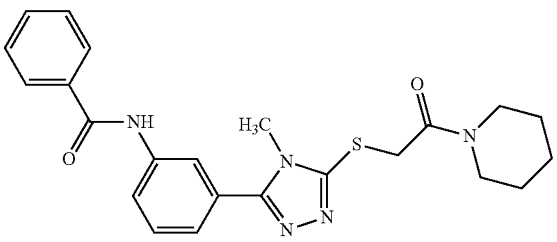

Compound 28

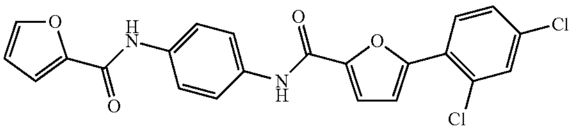

The methods described herein include a method of treating protein folding disorders (e.g., cystic fibrosis) in a subject. These methods include the step of administering to the subject a compound of the structures described herein. Additional steps can be included in the method described herein. For example, the methods can further include the steps of selecting a subject with a protein folding disorder, such as cystic fibrosis, and administering to the subject one or more of the CFTR correctors described herein.

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I-XII and Compounds 1-28 include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatograpy (HPLC) or thin layer chromatography.

One or more of the compounds described herein or pharmaceutically acceptable salts or prodrugs thereof can be provided in a pharmaceutical composition comprising a pharmaceutical carrier. Furthermore, the one or more compounds described herein can be combined with other agents, including treatments for lung, digestive, hepatic, and biliary tract related diseases and disorders. For example, in the case of cystic fibrosis, the compounds described herein can be combined with mucus thinning drugs (e.g., dornase alfa, N-Acetyl cysteine, and hypertonic saline), bronchodilators (e.g., metaproterenol sulfate, pirbuterol acetate, salmeterol, albuterol, and terbutaline sulfate), P2Y2-receptor agonists (e.g., denufosol), and agents that target nonsense mutations (e.g., PTC124). Further examples of additional agents that can be combined with the compounds described herein include antibiotics (e.g., aminoglycosides, antipseudomonal penicillins, and cephalosporins), antimicrobial drugs (e.g., rifabutin), ethambutol, clarithromycin, clofazimine, aztreonam, steroidal and nonsteroidal anti-inflammatory drugs (e.g., ibuprofen and prednisone), pentoxifylline, dornase alfa, or ursodeoxycholic acid.

The one or more compounds described herein can be provided as pharmaceutical compositions administered in combination with one or more other therapeutic or prophylactic agents. As used throughout, a therapeutic agent is a compound or composition effective in ameliorating a pathological condition. Illustrative examples of therapeutic agents include, but are not limited to, chemotherapeutic agents, antiviral agents, anti-opportunistic agents, antibiotics, and immunostimulatory agents. Optionally, more than one therapeutic agent is administered in combination with the provided compositions.

The one or more compounds described herein, with or without additional agents, can be provided in the form of an inhaler or nebulizer for inhalation therapy. As used herein, inhalation therapy refers to the delivery of a therapeutic agent, such as the compounds described herein, in an aerosol form to the respiratory tract (i.e., pulmonary delivery). Additional inhalants useful for delivery of the compounds described herein include intra-oral sprays, mists, metered dose inhalers, and dry powder generators (See Gonda, *J. Pharm. Sci.* 89:940-945, 2000, which is incorporated herein by reference in its entirety, at least, for inhalation delivery methods taught therein).

Depending on the intended mode of administration, the pharmaceutical composition can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, aerosols, and inhalants (e.g., intra-oral sprays, mists, metered dose inhalers, nebulizers, and dry powder generators). The compounds described herein or pharmaceutically salts or prodrugs thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein).

Administration of compounds described herein or pharmaceutically acceptable salts or prodrugs thereof can be carried out using therapeutically effective amounts of the compounds described herein or pharmaceutically acceptable salts or prodrugs thereof for periods of time effective to treat neurological disorders. The effective amount of the compounds described herein or pharmaceutically acceptable salts or prodrugs thereof can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In the methods described herein, the subjects treated can be further treated with one or more additional agents. The one or more additional agents and the compounds described herein or pharmaceutically acceptable salts or prodrugs thereof can be administered together in a single composition (e.g., as an admixture) or in separate compositions in any order, including simultaneous administration, as well as temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially. By treatment, treating, or treat is meant a reduction in one or more signs or symptoms or an improvement in the clinical state of the subject being treated for a disease or disorder (e.g., cystic fibrosis). For example, reduced numbers of infections or hospitalizations, reduction in respiratory or gastrointestinal symptoms, improved nutritional status, or improved pulmonary function indicate effective treatment.

As described above, the compounds described herein are useful in the treatment of protein folding disorders. Examples of protein folding disorders include cystic fibrosis; neurodegenerative diseases such as Alzheimer's disease, Parkinson's disease, Creutzfeld-Jakob disease, Kuru, GSS disease, Huntington's disease, Polyglutamine diseases, Prion disease, Bovine Spongiform Encephalopathy (BSE), Amyotrophic Lateral Sclerosis, Alexander's disease, Primary Systemic Amyloidosis, Secondary Systemic Amyloidosis, Senile Systemic Amyloidosis, and Amyloidosis in senescence; ocular diseases such as Cataract, Retinitis Pigmentosa, and Macular Degeneration; and other diseases such as Islet amyloid, Medullar Carcinoma of the Thyroid, Hereditary Renal Amyloidosis, Hemodialysis-related amyloidosis, Desmin-related Cardiomyopathy, Charcot-Marie Tooth disease, diabetes insipidis, diabetes insipidis, alpha1 antitrypsin deficiency, Fabry's disease, Gaucher's disease, Pompe's disease, and Charcot-Marie Tooth disease.

Additionally, a method of screening for a compound for treating cystic fibrosis (i.e., a CFTR corrector) is provided. Compounds that are suitable for treating cystic fibrosis have the ability to rescue delF508-CFTR. In addition, the compounds are effective on endogenously expressed delF508-CFTR. Further, the compounds are stable and the effects persist in serum-containing medium. The method for screening for CFTR correctors involves the steps of contacting a cell with the compound to be screened and detecting rescue of halide efflux from the cell. The halide efflux rescue indicates that the compound is useful in treating cystic fibrosis (i.e., the compound is a CFTR corrector). The method can be performed in vitro or in vivo. The method provides an effective and reliable means of screening for CFTR correctors.

The cell models used in other methods of identifying CFTR correctors have employed low temperature, chemical chaperones such as glycerol, 4-phenylbutyrate, DMSO, and overexpression of CFTR in a transduced Fisher rat thyroid cell line as the model, whereas the present methods do not require, and optionally exclude, over-expression of CFTR, low temperature, and chemical chaperones, variables that can distort the results.

The cells useful with the methods described herein endogenously express a CFTR mutation (e.g., the delF508-CFTR mutation). In some examples, the cell can be a human airway epithelial cell (e.g., CFBE41o-cells). CFBE41o-cells are human airway epithelial cells on a delF508-CFTR homozygous background. An example of cells useful with the methods described herein includes cells that do not overexpress the CFTR mutation.

The step of detecting a rescue of halide efflux from the cell can be monitored using the halide quenched dye 6-methoxy-N-(3-sulfopropyl)-quinolinium (SPQ, Molecular Probes Inc., Eugene, Oreg.), as described below in Example 1. In some examples, the halide efflux monitored can be chloride efflux.

The method of screening for a compound for treating cystic fibrosis as described herein can be performed with multiple doses of the compound as shown in Example 2. The method of screening for a compound for treating cystic fibrosis as described herein can further include determining CFTR immunoprecipitation, as described in Example 3. In addition, the method of screening for a compound for treating cystic fibrosis as described herein can also include determining CFTR glycosylation, as described in Example 4. CFTR glycosylation is determined by monitoring the two N-linked glycosylation sites on the fourth extracellular loop of CFTR. The immature, ER form shows as Band B on an SDS-PAGE gel, while a fully processed, mature form appears as Band C on an SDS-PAGE gel. Agents that correct ΔF508 CFTR promote Band C formation. Thus, CFTR glycosylation can be used to monitor correction.

The CFTR glycosylation assay can be used to determine whether the protein is in a post-Golgi compartment. However, this assay does not determine whether the protein is on the cell surface. Thus, the CFTR glycosylation assay can be used in conjunction with surface biotinylation, which does display whether the protein is on the cell surface. The CFTR glycosylation assay and surface biotinylation assays can used as complementary approaches for illustrating the effectiveness of ΔF508 CFTR correction.

In general, compounds useful for treating cystic fibrosis can be identified from large libraries of natural products or synthetic (or semi-synthetic) extracts or chemical libraries according to methods known in the art. The precise source of test extracts or compounds is not critical to the screening procedure(s). Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries and libraries of natural compounds in the form of bacterial, fungal, plant, and animal extracts are commercially available. In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

The examples below are intended to further illustrate certain aspects of the methods and compounds described herein, and are not intended to limit the scope of the claims.

EXAMPLES

Example 1

SPQ High Throughput Screening Assay

A schematic showing a general approach for identifying delF508-CFTR correctors is shown in FIG. 1. In FIG. 1, a non-CF ciliated airway epithelial cell is shown at left and a CF airway cell is shown at right. In CF, chloride secretion is often lost and sodium absorption becomes hyperactive. As a result, water is absorbed too vigorously in CF due to osmotic forces. Dehydration of the airway surface liquid causes a "domino effect" of problems with ciliary beat, mucociliary clearance, accumulation of dehydrated mucus and infection with opportunistic bacteria. The green and orange color depicts non-mucoid and mucoid *Pseudomonas aeruginosa* bacteria, respectively, that have taken hold and are accumulating within the thickened mucus in progressing CF pulmonary disease. The approach for discovering delF508-CFTR correctors is shown in FIG. 1 in the right panel.

Figure 2:
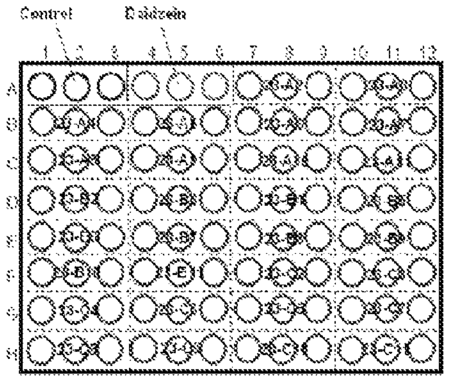
FIG. 2 is a schematic of a microtiter plate used for the SPQ high throughput screening assay.

To perform the SPQ high throughput screening assay, CFBE41o-cells are seeded into 96-well microtiter plates and are loaded with the fluorescent halide-sensitive dye, SPQ, in serum-containing culture medium. Certain wells are loaded with daidzein or hesperetin, which are known flavanoid positive control corrector molecules. For example, as shown in FIG. 2, daidzein is loaded into wells corresponding to A4, A5, and A6. The test compounds are loaded into wells and are tested in triplicate wells (e.g., wells A7, A8, and A9 in FIG. 2) at a 10 nM dose and incubated over 48 hours at room temperature. During the 48 hour period, SPQ is absorbed. Plates are washed in a sodium chloride (NaCl) based Ringer and read once over two minutes to set the baseline SPQ fluorescence activity. Then, NaCl is replaced by sodium nitrate ($NaNO_3$) based Ringer. The plates are read twice over four minutes. The primary high throughput screen (HTS) data are analyzed to detect any function of rescued delF508-CFTR under basal conditions. $NaNO_3$ based Ringer containing genistein (25 μM) is then added and the plates are read five times over ten minutes to determine the delF508-CFTR activity that can be rescued and active on the cell surface. Genistein is then removed, and $NaNO_3$ based Ringer is maintained. The plate is read up to two times to complete the SPQ HTS assay.

Example 2

Dose Response Assessment

Figure 3:
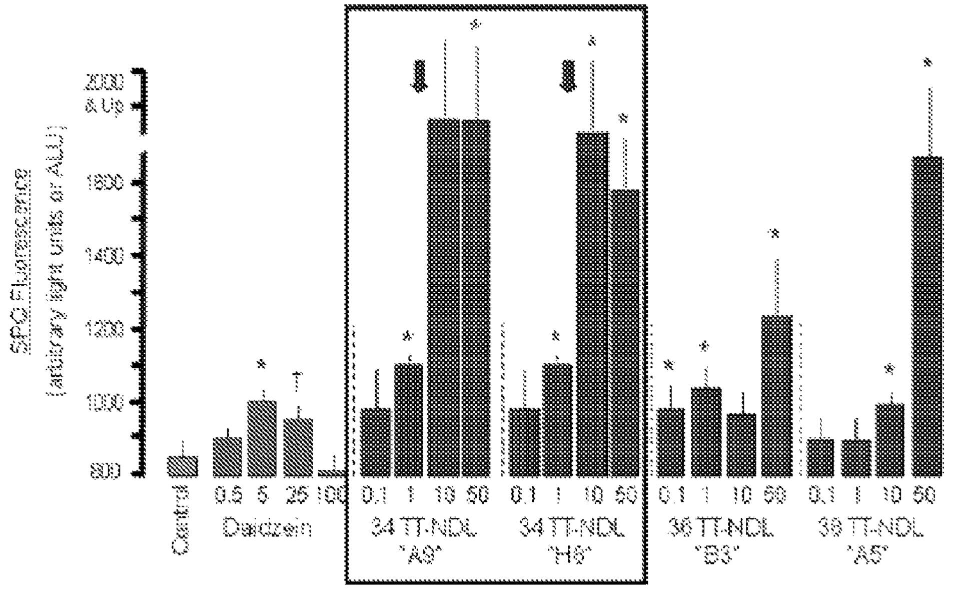
FIG. 3 is a graph demonstrating the dose-response data for daidzein and putative CFCL hit compounds by way of example.

The method described in Example 1 is repeated with doses of the test compound of 0.1 μM, 1 μM, 10 μM, and 50 μM in Dulbecco's Modified Eagle Medium (DMEM) with 10% fetal bovine serum (FBS) for 48 hours at 37° C. Unaltered CFBE41o-cells are used as the model. A Western blot analysis of the lysates (10-50 ng total protein) will be performed using the MM13-4 antibody for human CFTR to monitor changes in the CFTR protein. The most effective concentrations and time courses (12-96 h) are determined. By way of example, a graph showing the dose response results for exemplary compounds is provided in FIG. 3. Daidzein was used as the control.

Example 3

CFTR Immunoprecipitation

CFTR is immunoprecipitated under mild detergent conditions (1% digitonin, 2.5 mM HEPES, 10.0 mM $CaCl_2$, pH 7.6). The isolated protein complexes are run on SDS-PAGE gels and analyzed by mass spectroscopy. The CFBE41o-control cells are lysed in 2% digitonin (2.5 mM HEPES, 10.0 mM $CaCl_2$, pH 7.6). All lysis buffers are supplemented with a protease inhibitor cocktail (Complete Mini, Roche, Nutley, N.J.). CFTR is immunoprecipitated using Protein A-immobilized agarose beads and antibodies to the C-terminus of CFTR or to the second nucleotide-binding domain. The antibodies are covalently coupled to agarose beads before use (PROFOUND Mammalian Co-IP Kit, Pierce, Rockford, Ill.). The immunoprecipitated CFTR complexes are run on gels, and the interacting proteins are analyzed by mass spectroscopy.

Example 4

CFTR Surface Biotinylation

The cell surfaces are biotinylated and the cells are homogenized. The membrane fragments are isolated and lysed in co-immunoprecipitation buffer. The biotinylated protein complexes are captured with avidin, followed by coupling of the anti-CFTR antibody to agarose beads. The intact protein complexes are separated following CFTR immunoprecipitation during electrophoresis. Cells with no biotin and cells biotinylated but without CFTR expression are used as the controls.

Example 5

CFTR Glycosylation

Cells are lysed in RIPA buffer (50 mM Tris-HCl, pH 7.4, 150 mM NaCl, 1% NP-40, 0.5% Deoxycholic Acid, 0.1% SDS) plus a cocktail of protease inhibitors (Roche; Basel, Switzerland). Protein concentrations in the cell lysates are measured by BCA Protein Assay using BSA as standard (Pierce; Rockford, Ill.). Proteins (25 μg) are resolved on a 8% SDS-PAGE gel and transferred to PDVF membranes. Total CFTR in the lysate is detected by immunoblotting using a specific CFTR antibody (MM13-4 from Upstate, 1:500 dilution).

Example 6

Biochemical CFTR Rescue with delF508-CFTR Corrector Ligands

Figure 4:
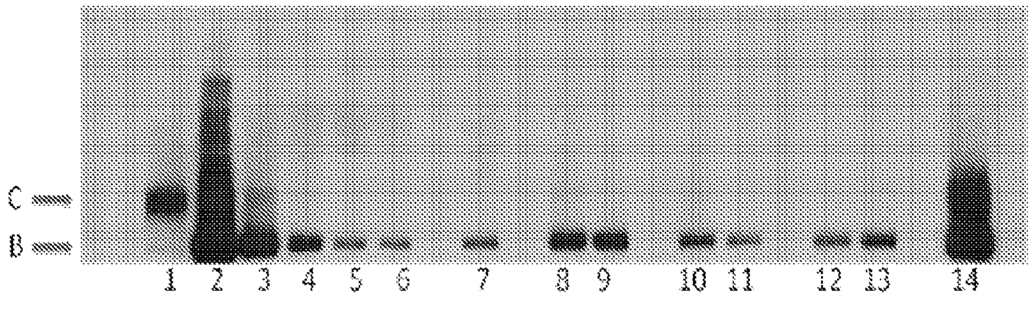
FIG. 4 is a Western blot demonstrating the delF508 CFTR rescue in CF human airway epithelial cells using Compound 43-H11 and related analogs that were validated hit corrector compounds, by way of example. Existing known Corrector drugs 4 and 17, WT-CFTR and DMSO served as the controls. Lane 1 shows the WT-CFTR control. Lanes 2, 3, 4, 5, and 6 represent Compound 43-H11 at concentrations of 10 μM, 1 μM, 100 nM, 10 nM, and 1 nM, respectively. Lane 7 represents the DMSO control. Lanes 8 and 9 represent 10 μM of Corrector 4 and Corrector 7, respectively. Lanes 10 and 11 represent 1 μM of Corrector 4 and Corrector 7, respectively. Lanes 12 and 13 represent 100 nM of Corrector 4 and Corrector 7, respectively. Lane 14 represents the low temperature (27° C.) control.

The compounds were then subjected to a biochemical assay to define which hit compounds rescued the band B core glycosylated endoplasmic reticulum (ER) form of delF508-CFTR within the cell interior into the maturely glycosylated band C form within the secretory pathway for proteins and within the plasma membrane (FIG. 4). Effective compounds stabilized the band B form of CFTR and caused more of this form to accumulate at the level of the ER. The most effective compounds caused the band C form to appear.

By way of example, compound 43H11, a validated CFTR Corrector compound, was added to CFBE41o-ΔF cells in OptiMEM-1 containing 2% serum in amounts of 10 μM, 1 μM, 100 nM, 10 nM, and 1 nM (see FIG. 4). DMSO, Corrector 4, Corrector 17, and WT-CFTR served as controls. A low temperature (27° C.) correction control was also used. Correctors 4 and 17 are known CFTR correctors available to the CF research community. The media and compound were replenished at 24 hours during the 48 hour treatment. The 1 μM dose of Compound CB 43-H11 was superior to the 10 μM doses of Corrector 4 and Corrector 17, two agents previously found to correct delF508. The 10 μM dose of CB 43-H11 provided similar levels of Band C to that of a low temperature correction control and a WT-CFTR expressing cell control. The delF508-CFTR mutation can be rescued from the ER with low temperature incubation for 48 hours.

Figure 5:
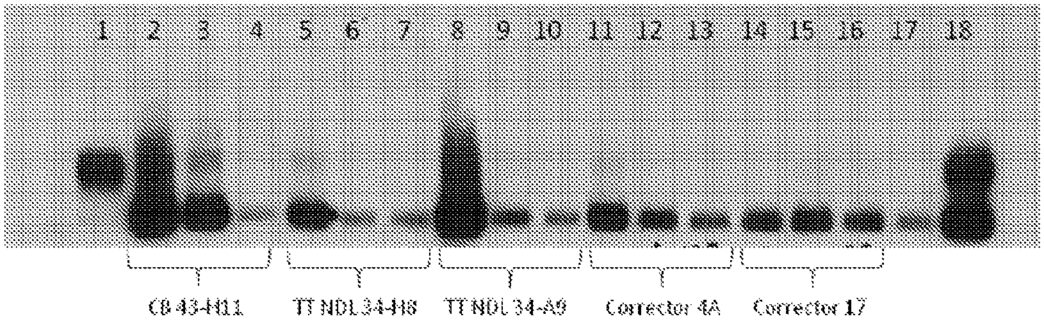
FIG. 5 is a Western blot demonstrating the delF508 CFTR rescue in CF human airway epithelial cells using Compounds 43-H11 and related analogs, TT NDL 34-H8, and TT NDL 34-A9. Existing known Corrector drugs 4 and 17, WT-CFTR, DMSO, and low temperature (27° C.) served as the controls. Lane 1 shows the WT-CFTR control. Lanes 2, 3, and 4 represent Compound 43-H11 at concentrations of 10 μM, 1 μM, and 100 nM, respectively. Lanes 5, 6, and 7 represent Compound 34-H8 at concentrations of 10 μM, 1 μM, and 100 nM, respectively. Lanes 8, 9, and 10 represent Compound 34A9 at concentrations of 10 μM, 1 μM, and 100 nM, respectively. Lanes 11, 12, and 13 represent Corrector 4 at concentrations of 10 μM, 1 μM, and 100 nM, respectively. Lanes 14, 15, and 16 represent Corrector 17 at concentrations of 10 μM, 1 μM, and 100 nM, respectively. Lane 17 represents the DMSO control. Lane 18 represents the low temperature (27° C.) control.

Compounds 43-H11, TT NDL 34-H8, and RR NDL 34-A9 were also tested in the biochemical rescue assay. Each compound was tested at 10 μM, 1 μM, and 100 nM. DMSO, Corrector 4, Corrector 17, WT-CFTR, and low temperature (27° C.) served as the controls. (see FIG. 5). The experiments were performed in 10% serum containing medium using the method as described above. The data demonstrate that the corrector compounds described herein are effective independent of serum protein.

Example 7

Electrical Measurements of Transepithelial Resistance

Electrical assay were also performed to determine the functional rescue of delF508-CFTR to the apical cell membrane in a polarized epithelium using the compounds described herein. These experiments were performed using a mouse mixed lung epithelial cell line engineered from the delF508-CFTR mouse (FIG. 6). Compounds 99-A4 and 99-H7 were tested at 2 μM doses. DMSO, WT-CFBE, and delF-CFBE at 37° C. and 27° C. served as the controls.

Figure 6A:
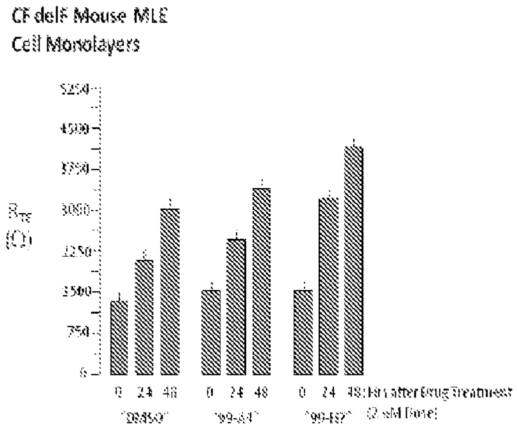
FIG. 6A is a graph showing the $R_{TE}$ measurements of Compounds 99-A4 and 99-H7 at 2 μM doses. CF delF mouse MLE cell monolayers were used for the tests.
Figure 6B:
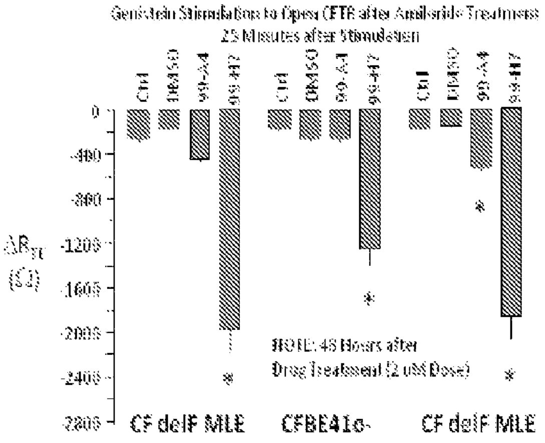
FIG. 6B is a graph showing the $R_{TE}$ measurements of Compounds 99-A4 and 99-H7 at 2 μM doses using CF delF mouse MLE cell monolayers, CLBE41o-, and CF delF MLE cells treated with amiloride and genistein.
Figure 6C:
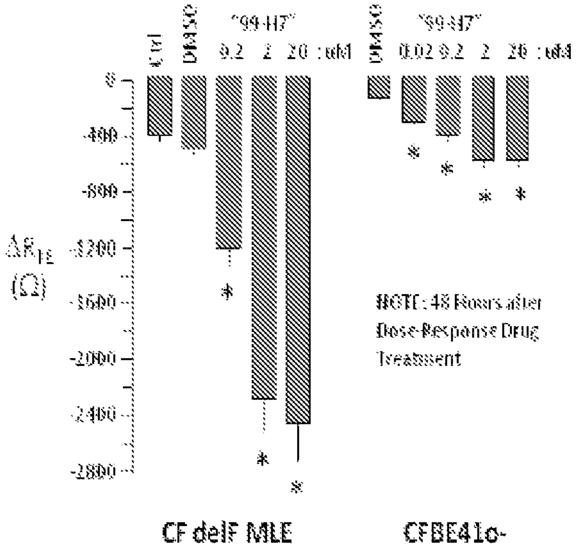
FIG. 6C is a graph of $R_{TE}$ measurements demonstrating the dose-response relationships for Compound 99-H7 using CF delF MLE and CFBE41o-cell lines.

Only high-resistance cell monolayers (>3,000 Ohms per $cm^2$) were used in the experiments. The $R_{TE}$ measurements shown in FIG. 6A demonstrate that the cell monolayers continue to "tighten" or develop in the presence of delF508-CFTR corrector small molecules. In the presence of amiloride (100 μM), used to block ENaC sodium channels (a step that increased $R_{TE}$), genistein (25 μM) was added to selectively open any delF508-CFTR chloride channels in the apical cell membrane (FIG. 6B). A significant decrease in $R_{TE}$ suggests that delF508-CFTR chloride channels are opening in the membrane. $R_{TE}$ measurements under voltage clamping show that small molecule 99-A7 is particularly potent. Dose-response relationships showing that 99-A7 rescues functional delF508-CFTR at nanomolar to low micromolar doses after a 48 hour treatment are provided in FIG. 6C.

Figure 6D:
FIG. 6D is a Western blot demonstrating the rescue of Band C for Compound 99H7 and Compound 99A4.

In this electrical assay on polarized CF human airway epithelial cell monolayers, correction of the Cl— transport defect was shown using a drop in transepithelial resistance as an indicator of rescued delF508-CFTR Cl— channels opening at the cell surface. Compound CB 99-H7 worked well while CB 99-A4 was less effective. Importantly, the transepithelial resistance continued to improve and the monolayers became more mature in the presence of these compounds. The rescue of band C blot is also shown for these compounds (FIG. 6D).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A method for the treatment of a protein folding disorder in a subject, comprising:

administering to the subject a CFTR corrector compound, wherein the CFTR corrector compound has the following structure:

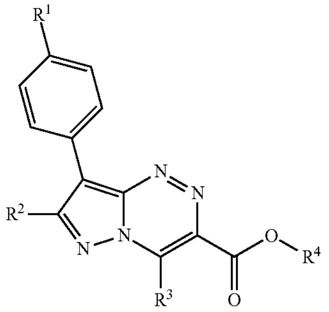

or a pharmaceutically acceptable salt thereof, wherein:

$R^1$ is hydrogen, halogen, alkoxy, substituted or unsubstituted amino, or substituted or unsubstituted alkyl; and $R^2$, $R^3$, and $R^4$ are each independently substituted or unsubstituted alkyl.

2. The method of claim 1, wherein the protein folding disorder is cystic fibrosis.

3. The method of claim 1, wherein $R^1$ is chloro, fluoro, or methoxy.

4. The method of claim 1, wherein $R^2$ is methyl.

5. The method of claim 1, wherein $R^3$ is methyl.

6. The method of claim 1, wherein $R^4$ is methyl or ethyl.

7. The method of claim 1, wherein the compound is

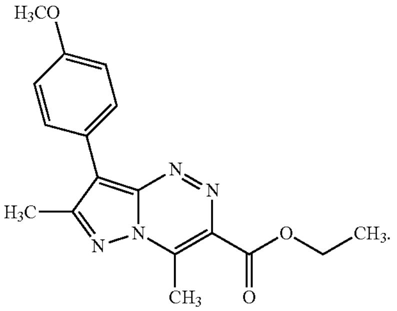

8. The method of claim 1, wherein the compound is

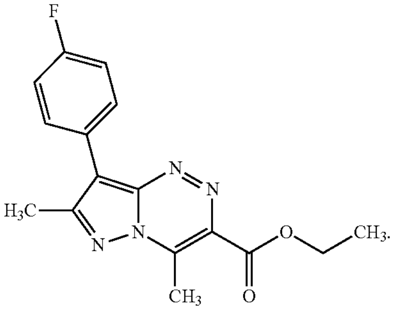

9. The method of claim 1, wherein the compound is

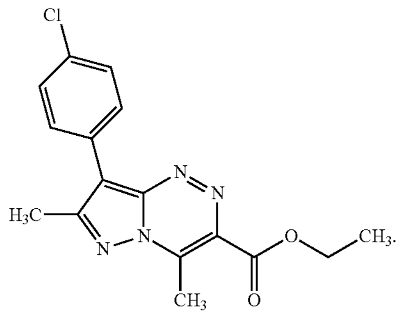

10. The method of claim 1, wherein the compound is

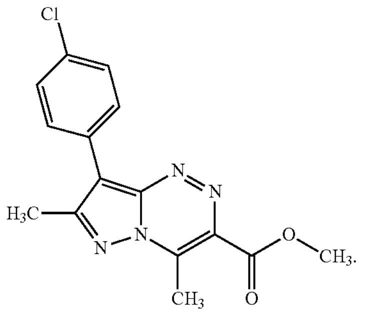

11. A method for the treatment of a protein folding disorder in a subject, comprising:

administering to the subject a CFTR corrector compound, wherein the CFTR corrector compound has the following structure:

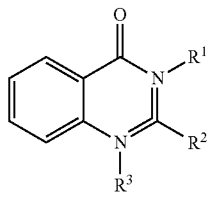

or a pharmaceutically acceptable salt thereof, wherein:

$R^1$ and $R^3$ are independently absent or each independently selected from hydrogen or substituted or unsubstituted alkyl;

$R^2$ is substituted or unsubstituted amino, substituted or unsubstituted thio, or substituted or unsubstituted heterocycloalkyl; and ⎓ is a single bond or double bond, wherein two double bonds are not adjacent, wherein optionally $R^1$ and $R^2$ are combined to form a substituted or unsubstituted aryl or substituted or unsubstituted heteroaryl.

12. A method for the treatment of a protein folding disorder in a subject, comprising:

administering to the subject a CFTR corrector compound, wherein the CFTR corrector compound has the following structure:

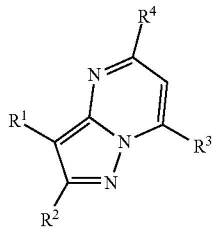

or a pharmaceutically acceptable salt thereof, wherein:

$R^1$ is hydrogen or substituted or unsubstituted carbonyl;

$R^2$ is hydrogen, carboxyl, or substituted or unsubstituted aryl;

$R^3$ is hydrogen, hydroxyl, trifluoromethyl, or substituted or unsubstituted alkyl; and $R^4$ is hydrogen, substituted or unsubstituted alkyl, or substituted or unsubstituted aryl.

13. A method for the treatment of a protein folding disorder in a subject, comprising:

administering to the subject a CFTR corrector compound, wherein the CFTR corrector compound has the following structure:

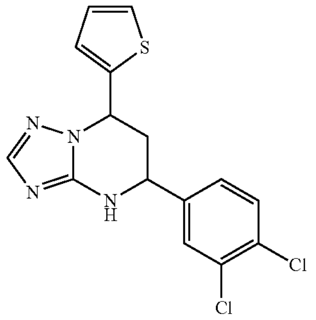 [SMILES: Clc1ccc(C2CC(c3cccs3)n3ncnc3N2)cc1Cl]

or a pharmaceutically acceptable salt thereof.

14. A method for the treatment of a protein folding disorder in a subject, comprising:

administering to the subject a CFTR corrector compound, wherein the CFTR corrector compound has the following structure:

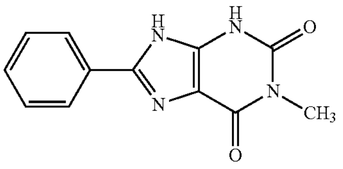 [SMILES: Cn1c(=O)[nH]c2[nH]c(-c3ccccc3)nc2c1=O]

or a pharmaceutically acceptable salt thereof.

* * * * *